(12) United States Patent
Sano et al.

(10) Patent No.: US 8,679,421 B2
(45) Date of Patent: Mar. 25, 2014

(54) DISPENSING DEVICE AND ANALYZER

(75) Inventors: Minoru Sano, Hitachinaka (JP);
Kazutoshi Onuki, Hitachinaka (JP);
Yoshiyuki Shoji, Mito (JP); Isao Yamazaki, Ryugasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1 day.

(21) Appl. No.: 13/388,451

(22) PCT Filed: Jul. 15, 2010

(86) PCT No.: PCT/JP2010/062010
§ 371 (c)(1),
(2), (4) Date: Feb. 17, 2012

(87) PCT Pub. No.: WO2011/030616
PCT Pub. Date: Mar. 17, 2011

(65) Prior Publication Data
US 2012/0156098 A1    Jun. 21, 2012

(30) Foreign Application Priority Data

Sep. 11, 2009  (JP) .................................. 2009-210725

(51) Int. Cl.
*B01L 3/02*  (2006.01)
*G01L 21/00*  (2006.01)

(52) U.S. Cl.
USPC ........... 422/501; 422/509; 422/511; 422/518; 422/519; 422/521; 422/522; 422/63; 422/64; 422/68.1; 73/863.32; 73/864; 73/864.01; 73/864.02; 73/864.11; 73/864.13; 73/864.16; 73/864.21

(58) Field of Classification Search
USPC .................. 422/63–68.1, 500–501, 509, 511, 422/517–519, 521–522; 73/863.32, 864, 73/864.01, 864.02, 864.11, 864.13, 73/864.16, 864.21

See application file for complete search history.

(56) References Cited

U.S. PATENT DOCUMENTS 5,102,623 A    4/1992  Yamamoto et al.
5,125,748 A *  6/1992  Bjornson et al. .............. 356/414
(Continued)

FOREIGN PATENT DOCUMENTS

JP    01-097865    4/1989
JP    1-97865      4/1989
(Continued)

OTHER PUBLICATIONS

JP office action of Appln. No. 2009-210725 dated Jul. 10, 2012.
(Continued)

*Primary Examiner* — Brian R Gordon
(74) *Attorney, Agent, or Firm* — Antonelli, Terry, Stout & Kraus, LLP.

(57) ABSTRACT

A dispensing device and an analyzer capable of improving dispensing accuracy as well as improving jamming detection accuracy can be realized by having a short distance between a syringe and a suction tip. The dispensing device 10 includes an upper fixed unit 10A, a lower movable unit 10B which is connected to the upper fixed unit 10A, the movable unit being relatively movable with respect to the upper fixed unit 10A, and a Z-axis movement mechanism 55Z which moves the upper fixed unit to and fro. A syringe 4 and a plunger 13 are held by the upper fixed unit 10A. A tip nozzle 8 is attached to the lower movable unit 10B. An interior space of the syringe 4 and an interior space of the tip nozzle 8 are connected with each other by a connection tube 1 having flexibility.

19 Claims, 20 Drawing Sheets

(56) References Cited

U.S. PATENT DOCUMENTS

| | | | | |
|---|---|---|---|---|
| 5,158,748 | A * | 10/1992 | Obi et al. | 422/511 |
| 5,264,182 | A * | 11/1993 | Sakagami | 422/63 |
| 5,525,515 | A * | 6/1996 | Blattner | 436/49 |
| 5,948,359 | A * | 9/1999 | Kalra et al. | 422/65 |
| 6,495,106 | B1 * | 12/2002 | Kalra et al. | 422/510 |
| 6,868,875 | B2 * | 3/2005 | De Beukeleer et al. | 141/130 |
| 7,160,511 | B2 * | 1/2007 | Takahashi et al. | 422/504 |
| 7,227,018 | B2 * | 6/2007 | Shoji et al. | 536/25.41 |
| 7,344,048 | B2 | 3/2008 | Ueda et al. | |
| 7,618,589 | B2 * | 11/2009 | Toi et al. | 422/561 |
| 8,354,078 | B2 * | 1/2013 | Shohmi et al. | 422/511 |
| 8,383,039 | B2 * | 2/2013 | Zhou et al. | 422/63 |
| 8,394,635 | B2 * | 3/2013 | Key et al. | 436/43 |
| 2005/0194394 | A1 | 9/2005 | Ueda et al. | |

FOREIGN PATENT DOCUMENTS

| | | |
|---|---|---|
| JP | 4-201088 | 7/1992 |
| JP | 2003-344427 | 3/2003 |
| JP | 2003-344427 | 12/2003 |
| JP | 2005-207850 | 8/2005 |
| JP | 2007-139469 | 6/2007 |

OTHER PUBLICATIONS

JP Notification of Transmittal of the International Preliminary Report on Patentability of International Appln. No. 2010/062010 dated Apr. 19, 2012 in English.

US 5,102,823, 04/1992, Yamamoto at al. (withdrawn)

* cited by examiner

DISPENSING DEVICE AND ANALYZER

TECHNICAL FIELD

The present invention relates to a dispensing device and an analyzer which perform the suction/discharge of liquid by operating a syringe, and in particular, to a dispensing device and an analyzer suitable for using air as pressure-transmitting fluid inside the syringe being used for the suction/discharge of liquid.

BACKGROUND ART

In conventional dispensing devices used for automatic analyzers for analyzing blood, etc., liquid such as sterile water is used as pressure-transmitting fluid inside a syringe being used for the suction/discharge of liquid. Since liquid has the property of hardly changing its volume in spite of changes in the pressure and/or temperature, the distance between the syringe and a nozzle for sucking/discharging liquid has little effect on the dispensing accuracy, irrespective of length. Thus, such dispensing devices are configured such that the syringe is generally set at a position apart from the nozzle of the dispensing device and connected to the nozzle with a long tube. However, facilities for supplying the liquid to the device and dumping liquid waste are necessary.

Meanwhile, the present inventors are developing an analyzer for genetic testing in these years and are examining the use of air for the pressure-transmitting fluid inside the syringe being used for the suction/discharge of liquid. When liquid is used as the pressure-transmitting fluid in a genetic testing device, the problem with contamination occurs since the liquid moves inside the nozzle used for the dispensing. Reduction of the effect of the contamination is especially required of genetic testing devices compared with other automatic analyzers for analyzing blood, etc.

However, in the case where air is used as the pressure-transmitting fluid, the change in the volume of the air caused by the change in the pressure/temperature is greater than that of liquid, and thus the distance between the syringe and a suction tip has to be reduced for improving the dispensing accuracy.

A known inspection device is contrived to reduce the distance between the syringe and the suction tip by placing the syringe inside the dispensing device (see FIG. 4 of Patent Literature 1, for example).

Prior Art Literature

Patent Literature
  Patent Literature 1: JP-2005-207850-A

SUMMARY OF THE INVENTION

Problem to be Solved by the Invention

Analyzers are generally equipped with a jamming detection function of detecting the contact of the suction tip with a container storing liquid, etc.

However, if the distance between the syringe and the suction tip is reduced, a mechanism for the jamming detection function (springs 22 and 23, rail 15a) has to be placed between a syringe supporting part 21 (supporting a syringe part 12) and a base part 14 (serving as the base of the dispensing device) as illustrated in FIG. 5 of Patent Literature 1.

In this case, the syringe part 12, including a motor 12c and a syringe pump 12b as shown in FIG. 4 of Patent Literature 1, is necessitated to be heavy. The jamming detection function needs to correctly detect minute displacement or force caused by the contact. If the syringe part 12 is heavy as in Patent Literature 1, the detection of minute displacement or force is difficult and the accuracy of the jamming detection is deteriorated.

It is therefore the primary object of the present invention to provide a dispensing device and an analyzer capable of improving the dispensing accuracy and the jamming detection accuracy by realizing a short distance between the syringe and the suction tip.

Means for Solving the Problem (1) In order to achieve the above object, the present invention provides a dispensing device for sucking in liquid from a container through an end of a nozzle or a tip replaceably attached to an end of a tip nozzle and discharging the sucked liquid into another container by use of pressure generated by movement of a plunger inserted into a syringe, comprising: a fixed unit; a movable unit which is connected to the fixed unit, the movable unit being relatively movable with respect to the fixed unit; and a movement mechanism which moves the fixed unit to and fro. The syringe and the plunger are held by the fixed unit. The tip nozzle or the nozzle is attached to the movable unit. The dispensing device comprises a connection tube having flexibility and connecting interior space of the syringe with interior space of the tip nozzle or the nozzle.

With such a configuration, the dispensing accuracy and the jamming detection accuracy can be improved by realizing a short distance between the syringe and the suction tip.

(2) Preferably, the above dispensing device (1) further comprises detecting means which detects relative movement between the fixed unit and the movable unit.

(3) Preferably, in the above dispensing device (2), the detecting means detects that the nozzle or the tip attached to the tip nozzle has contacted another object based on the relative movement between the fixed unit and the movable unit.

(4) Preferably, in the above dispensing device (2), the detecting means detects that the tip has been attached to the tip nozzle based on the relative movement between the fixed unit and the movable unit.

(5) Preferably, the above dispensing device (1) further comprises: a connection rod which slidably connects the movable unit to the fixed unit; and a spring which is arranged between the fixed unit and the movable unit. The lower end of the spring contacts the upper end of the movable unit and the upper end of the spring has a noncontact spring length to the lower end of the fixed unit in a state in which the movable unit is suspended by the fixed unit.

(6) Preferably, the above dispensing device (5) further comprises detecting means which detects relative movement between the fixed unit and the movable unit. The detecting means detects that the tip attached to the tip nozzle has contacted another object in a state in which the upper end of the spring contacts the lower end of the fixed unit. The detecting means detects that the tip has been attached to the tip nozzle in a state in which the spring has been compressed.

(7) Preferably, the above dispensing device (1) further comprises an elastic member which connects the movable unit to the fixed unit. The elastic member connects the movable unit to the fixed unit so that the movable unit is movable in at least two directions orthogonal to each other.

(8) Preferably, in the above dispensing device (1), air is used as pressure-transmitting fluid for transmitting the pressure generated by the syringe, and the dispensing device comprises a tip replaceably attached to the end of the tip nozzle.

(9) Preferably, in the above dispensing device (1), liquid is used as pressure-transmitting fluid for transmitting the pressure generated by the syringe.

(10) Preferably, in the above dispensing device (1), the movable unit is connected to the fixed unit so that edging relative to the fixed unit is possible.

(11) In order to achieve the above object, the present invention provides an analyzer comprising: a sample container holding part which holds a sample container storing a sample solution; a reagent container holding part which holds reagent containers storing reagents, respectively; a reaction container holding part which holds a reaction container; a dispensing device which sucks in the sample solution in the sample container and a prescribed sample solution in the reagent container and dispenses the solutions to the reaction container; and a detector which detects the result of a reaction occurring in the reaction container. The dispensing device includes: a fixed unit; a movable unit which is connected to the fixed unit, the movable unit being relatively movable with respect to the fixed unit; and a movement mechanism which moves the fixed unit to and fro. The syringe and the plunger are held by the fixed unit. The tip nozzle or the nozzle is attached to the movable unit. The dispensing device includes a connection tube having flexibility and connecting interior space of the syringe with interior space of the tip nozzle or the nozzle.

With such a configuration, the dispensing accuracy and the jamming detection accuracy can be improved by realizing a short distance between the syringe and the suction tip.

Effect of the Invention

According to the present invention, the dispensing accuracy and the jamming detection accuracy can be improved by realizing a short distance between the syringe and the suction tip.

MODE FOR CARRYING OUT THE INVENTION

Figure 1:
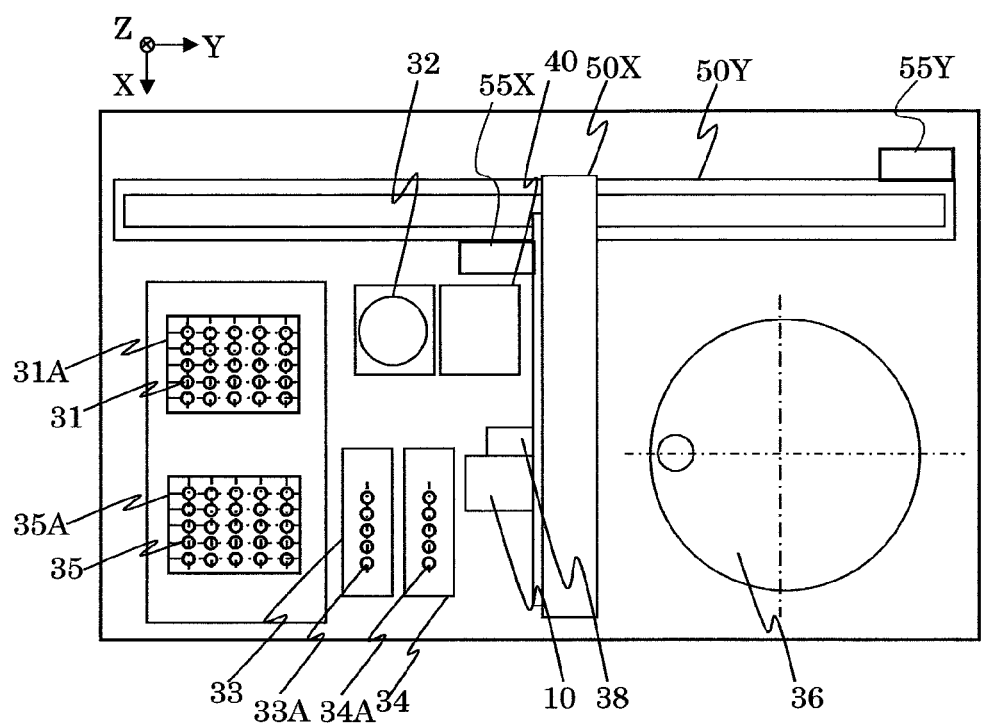
FIG. 1 is a plan view showing the configuration of an automatic analyzer equipped with a dispensing device in accordance with a first embodiment of the present invention.

In the following, the configuration and operation of a dispensing device in accordance with a first embodiment of the present invention will be described with reference to FIGS. 1-9. First, the configuration and operation of an automatic analyzer equipped with the dispensing device of this embodiment will be explained referring to FIG. 1. The following explanation will be given by taking a genetic testing device as an example of the automatic analyzer. FIG. 1 is a plan view showing the configuration of the automatic analyzer equipped with the dispensing device in accordance with the first embodiment of the present invention.

A plurality of tips 31 are held by a tip holding part 31A. The tip 31, made of resin, is attached to a tip nozzle at the end of the dispensing device 10 which will be explained later. The detailed configuration of the dispensing device 10 will be described later referring to FIGS. 2-4. The tip 31 of the disposable type is used and replaced for each sample (test object). The used tip 31 is discarded to a waste container 32.

A plurality of reagent containers 33 are held by a reagent container holding part 33A. The reagent containers 33 contain reagent solutions different from one another. From the reagent solution stored in each reagent container 33, a prescribed amount of the reagent solution is sucked in by the dispensing device 10. Meanwhile, a plurality of sample containers 34 are held by a sample container holding part 34A. Each sample container 34 contains a sample solution as a target of the inspection. From the sample solution stored in each sample container 34, a prescribed amount of the sample solution is sucked in by the dispensing device 10. A plurality of reaction containers 35 are held by a reaction container holding part 35A. Into each reaction container 35, the reagent liquid and the sample solution which have been sucked in by the dispensing device 10 are discharged.

An X arm 50X is attached to a Y rail 50Y to be movable in a Y direction. A Y-axis movement mechanism 55Y, including a stepping motor as a driving source, moves the X arm 50X in the Y direction along the Y rail 50Y. The dispensing device 10 and a gripper 38 are attached to the X arm 50X. An X-axis movement mechanism 55X, including a stepping motor as a driving source, moves the dispensing device 10 and the gripper 38 in an X direction along the X arm 50X. The dispensing device 10 and the gripper 38 are also movable in a Z direction.

Next, the overall flow of an analysis process executed by the analyzer of this embodiment will be described.

First, the dispensing of a reagent solution is executed.

The dispensing device 10 is positioned over a prescribed one of the tips 31 in the tip holding part 31A by moving the X arm 50X and the dispensing device 10 by operating the Y-axis movement mechanism 55Y and the X-axis movement mechanism 55X. Then, the dispensing device 10 descends in the Z direction, by which the tip 31 is attached to a tip nozzle at the end of the dispensing device 10 by press fitting.

Subsequently, the dispensing device 10 is positioned over a prescribed one of the reagent containers 33 in the reagent container holding part 33A by moving the X arm 50X and the dispensing device 10 by operating the Y-axis movement mechanism 55Y and the X-axis movement mechanism 55X. Then, the dispensing device 10 descends in the Z direction, by which the tip 31 at the end of the dispensing device 10 is inserted into the reagent container 33. At this position, a prescribed amount of the reagent solution is sucked in from the reagent container 33.

Subsequently, the dispensing device 10 is positioned over a prescribed one of the reaction containers 35 in the reaction container holding part 35A by moving the X arm 50X and the dispensing device 10 by operating the Y-axis movement mechanism 55Y and the X-axis movement mechanism 55X. Then, the dispensing device 10 descends in the Z direction, by which the tip 31 at the end of the dispensing device 10 is inserted into the reaction container 35. At this position, the reagent solution which has been sucked in is discharged into the reaction container 35.

Subsequently, the dispensing device 10 is positioned over the waste container 32 by moving the X arm 50X and the dispensing device 10 by operating the Y-axis movement mechanism 55Y and the X-axis movement mechanism 55X. At this position, the dispensing device 10 discards the used tip 31 to the waste container 32.

With the above operation, the dispensing of the reagent solution is finished.

Next, the dispensing of a sample solution is executed.

The dispensing device 10 is positioned over a prescribed one of the tips 31 in the tip holding part 31A by moving the X arm 50X and the dispensing device 10 by operating the Y-axis movement mechanism 55Y and the X-axis movement mechanism 55X. Then, the dispensing device 10 descends in the Z direction, by which the tip 31 is attached to the tip nozzle at the end of the dispensing device 10 by press fitting.

Subsequently, the dispensing device 10 is positioned over a prescribed one of the sample containers 34 in the sample container holding part 34A by moving the X arm 50X and the dispensing device 10 by operating the Y-axis movement mechanism 55Y and the X-axis movement mechanism 55X. Then, the dispensing device 10 descends in the Z direction, by which the tip 31 at the end of the dispensing device 10 is inserted into the sample container 34. At this position, a prescribed amount of the sample solution is sucked in from the sample container 34.

Subsequently, the dispensing device 10 is positioned over the aforementioned reaction container 35 in the reaction container holding part 35A (into which the reagent solution has been discharged) by moving the X arm 50X and the dispensing device 10 by operating the Y-axis movement mechanism 55Y and the X-axis movement mechanism 55X. Then, the dispensing device 10 descends in the Z direction, by which the tip 31 at the end of the dispensing device 10 is inserted into the reaction container 35. At this position, the sample solution which has been sucked in is discharged into the reaction container 35.

Subsequently, the dispensing device 10 is positioned over the waste container 32 by moving the X arm 50X and the dispensing device 10 by operating the Y-axis movement mechanism 55Y and the X-axis movement mechanism 55X. At this position, the dispensing device 10 discards the used tip 31 to the waste container 32.

With the above operation, the dispensing of the sample solution is finished.

Subsequently, the gripper 38 is positioned over the aforementioned reaction container 35 in the reaction container holding part 35A (into which the reagent solution and the sample solution have been discharged) by moving the X arm 50X and the gripper 38 by operating the Y-axis movement mechanism 55Y and the X-axis movement mechanism 55X. The gripper 38 descends, holds the reaction container 35, and ascends with the reaction container 35. Further, the gripper 38 is moved to a position over an incubator 40 by operating the Y-axis movement mechanism 55Y and the X-axis movement mechanism 55X. Then, the gripper 38 descends and sets the reaction container 35 on the incubator 40.

After a prescribed time has elapsed and the reaction between the sample solution and the reagent solution has proceeded sufficiently, the reaction container 35 is held by the gripper 38 and is transferred to a detection unit 36 by operating the Y-axis movement mechanism 55Y and the X-axis movement mechanism 55X.

The detection unit 36 determines the amounts of ingredients of the reaction solution (quantitative analysis). In the case of a genetic testing device, for example, a type of genome sequences as the target of the quantitative analysis are marked with a fluorescent pigment and corresponding fluorescence intensity is measured by the detector 36.

Figure 2:
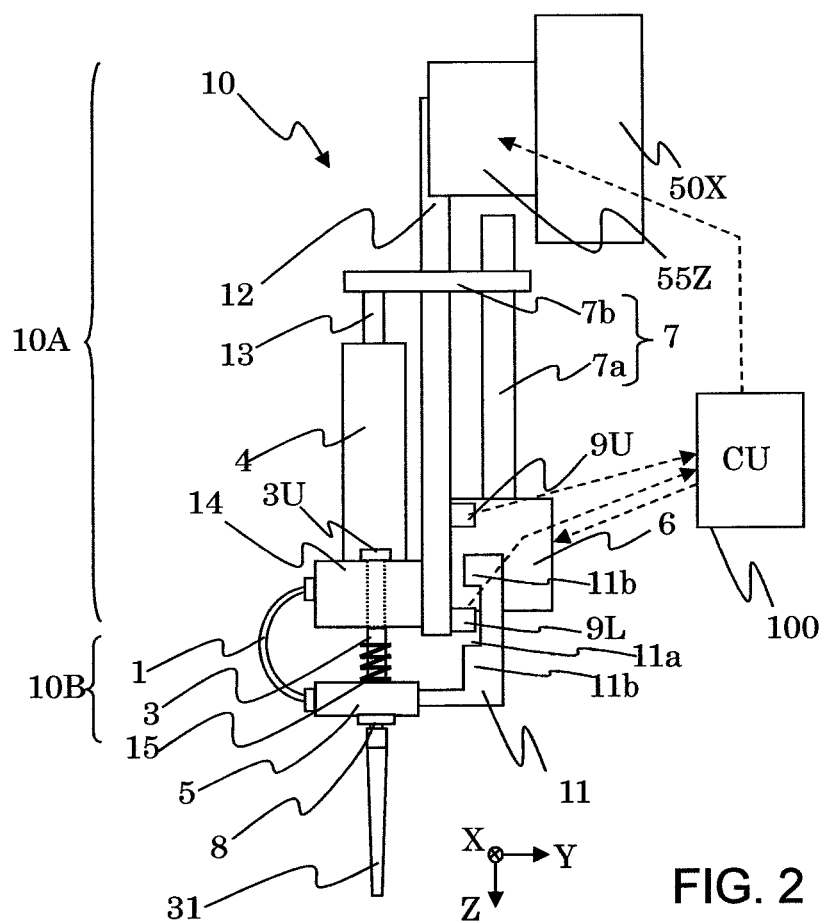
FIG. 2 is a front view showing the configuration of the dispensing device in accordance with the first embodiment of the present invention.
Figure 3:
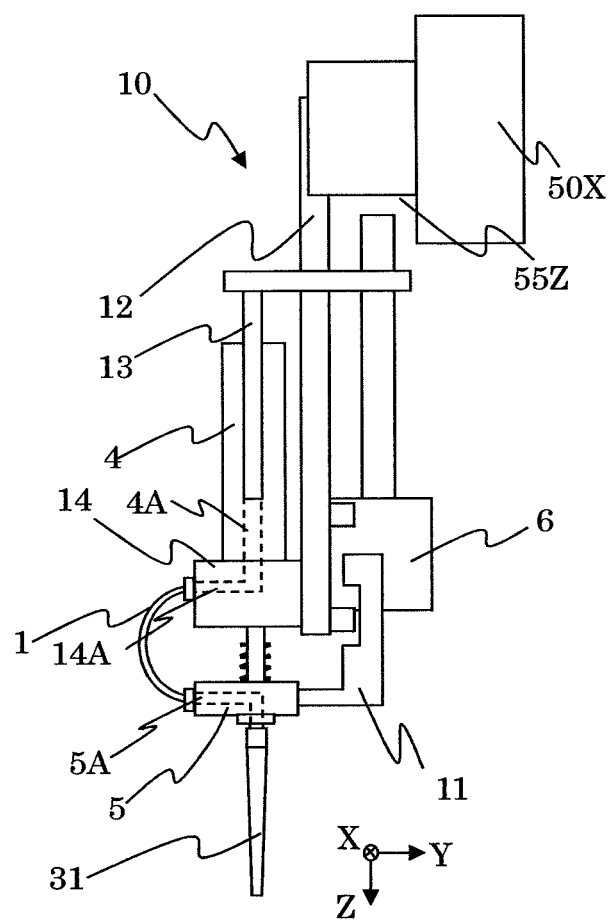
FIG. 3 is a front view showing the internal configuration of the dispensing device in accordance with the first embodiment of the present invention.
Figure 4:
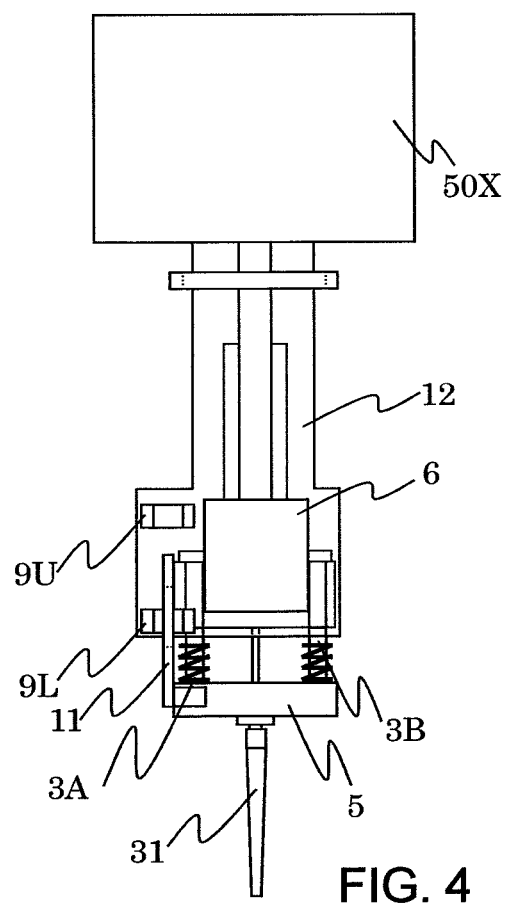
FIG. 4 is a side view showing the configuration of the dispensing device in accordance with the first embodiment of the present invention.

Next, the configuration of the dispensing device in accordance with this embodiment will be described referring to FIGS. 2-4. FIG. 2 is a front view showing the configuration of the dispensing device in accordance with the first embodiment of the present invention. FIG. 3 is a front view showing the internal configuration of the dispensing device in accordance with the first embodiment of the present invention. FIG. 4 is a side view showing the configuration of the dispensing device in accordance with the first embodiment of the present invention (right side view of FIG. 2). In the figures, the same reference characters represent the same component.

As shown in FIG. 2, a Z-axis movement mechanism 55Z is attached to the X arm 50X. The Z-axis movement mechanism 55Z is equipped with a stepping motor as a driving source and a feed screw. A syringe base 12 of the dispensing device 10 is fixed to a nut part of the feed screw. Thus, when the feed screw is rotated by the stepping motor, the feed screw moves straight and thereby moves the syringe base 12 in the Z-axis direction.

The dispensing device 10 is mainly composed of an upper fixed unit 10A and a lower movable unit 10B. The upper fixed unit 10A and the lower movable unit 10B are moved together in the Z-axis direction by the Z-axis movement mechanism 55Z. When the end of the lower movable unit 10B (lower end of the tip 31 in the example shown in FIG. 2) makes contact with a container, etc., the lower movable unit 10B can independently move relative to the upper fixed unit 10A.

First, the configuration of the upper fixed unit 10A will be explained. The upper fixed unit 10A mainly includes a hollow-body syringe 4, a driving source 6, a power converter 7, the syringe base 12, a plunger 13 and a syringe fixation member 14. The driving source 6, including a stepping motor, etc., is fixed to the syringe base 12. The converter 7 includes a ball screw 7a and a moving member 7b engaged with the ball screw 7a. When the ball screw 7a is driven and rotated by the driving source 6, the motion is converted to linear motion and the moving member 7b moves in the Z-axis direction. Incidentally, it is also possible to employ a slider engaged with the ball screw 7a and fix the moving member 7b to the slider. In order to improve the positional accuracy of the slider moving up and down, a linear guide may be attached to the syringe base 12.

The plunger 13 is fixed to the moving member 7b. The plunger 13, inserted into the syringe 4, moves to and fro inside the syringe 4 according to the normal/reverse rotation of the driving source 6. Since the upper part of the syringe 4 (i.e., the sliding interface between the syringe 4 and the plunger 13) is kept hermetic by a member like a seal piece, air does not leak out.

The lower end of the syringe 4 is hermetically fixed to the syringe fixation member 14. As shown in FIG. 3, a hollow part 4A inside the syringe 4 and a channel 14A formed inside the syringe fixation member 14 are connected with each other. Returning to FIG. 2, the syringe fixation member 14 is fixed to the syringe base 12. An upper photo interrupter 9U for tip attachment detection and a lower photo interrupter 9L for the jamming detection are fixed on the syringe base 12.

Next, the configuration of the lower movable unit 10B will be explained. The lower movable unit 10B mainly includes a tip holding part 5, a connection rod 3 and a spring 15. A tip nozzle 8, for firmly holding the replaceable tip 31 attached thereto by press fitting, is attached integrally to the tip holding part 5.

The connection rod 3 is made up of two rods 3A and 3B as shown in FIG. 4. The lower part of the connection rod 3 is fixed to the tip holding part 5. The upper part of the connection rod 3 is inserted into through holes formed in the syringe fixation member 14 so that the connection rod 3 can move up and down. The sliding interfaces between the connection rod 3 and the syringe fixation member 14 are provided with linear bearings for excellent lubrication. It is also possible to place members excelling in lubrication (e.g., fluoroplastic) instead of the linear bearings.

A channel 5A is formed inside the tip holding part 5 as shown in FIG. 3. The channel 5A of the tip holding part 5 and the channel 14A of the syringe fixation member 14 are hermetically connected with each other by a hollow connection tube 1. Inside the tip 31, a through hole is formed from the upper end to the lower end of the tip 31. The channel 5A of the tip holding part 5 is connected with the through hole inside the tip 31 via a hole inside the tip nozzle 8. Therefore, the hollow part 4A of the syringe 4 is connected to an opening part at the end of the tip 31 via the channel 14A of the syringe fixation member 14, the hollow part of the connection tube 1, the channel 5A of the tip holding part 5 and the through hole inside the tip 31. The connected space from the hollow part 4A of the syringe 4 to the opening part at the end of the tip 31 is filled with air as the pressure-transmitting fluid. Therefore, if the plunger 13 moves upward when the end of the tip 31 has been inserted into the reagent solution inside the reagent container, for example, the pressure inside the connected space drops and the reagent solution can be sucked in through the end of the tip 31. In contrast, if the plunger 13 moves downward when the reagent solution has been sucked into the tip 31, the pressure inside the connected space rises and the reagent solution previously sucked into the tip 31 is discharged from the opening part at the end of the tip 31.

It should be noted that no solution (sample solution, reagent solution) is sucked in up to the channel 5A of the tip holding part 5 since the amount of the sample solution or the reagent solution sucked in through the end of the tip 31 has been set smaller than the capacity of the through hole inside the tip 31. Therefore, the effect of contamination is eliminated by discarding the used tip 31 for each sample.

The connection tube 1 is made of a material enabling bendability/flexibly (e.g., fluoroplastic). Thus, the connected space described above is not blocked up even when the tip holding part 5 moves up and down. The shape of the connection tube 1 is not particularly restricted as long as the capacity inside the connection tube 1 does not change much between the normal state and the bent state. For example, either a cylindrical tube with a smooth surface or a bellows tube may be used. Further, if a preparation is made by sucking in liquid until the liquid exists in the tip holding part 5 and further sucking in air by driving the syringe with the dispensing nozzle end (tip) placed in the air, even the deformation of the connection tube 1 due to the bending is permissible as long as the change in the volume (capacity) is smaller than the volume of the air.

A stopper part 3U is attached to the upper end of the connection rod 3. In the state shown in FIG. 2, the stopper part 3U contacts the top of the syringe fixation member 14 and thereby prevents the tip holding part 5 from descending further. In the state of FIG. 2, the tip holding part 5, which has descended due to its own weight, is situated at the lowest point in its movable range due to the restriction on its downward movement by the stopper part 3U.

The spring 15 is arranged between the syringe fixation member 14 and the tip holding part 5 to surround the connection rod 3. In the state shown in FIG. 2, the stopper part 3U contacts the syringe fixation member 14 and the tip holding part 5 is suspended from the stopper part 3U. In this state, the lower end of the spring 15 contacts the top of the tip holding part 5 and a gap is formed between the upper end of the spring 15 and the syringe fixation member 14. In other words, in the state in which the lower movable unit 10B is suspended by the upper fixed unit 10A, the lower end of the spring 15 contacts the upper end of the lower movable unit 10B and the upper end of the spring 15 has a noncontact spring length to the lower end of the upper fixed unit 10A.

In a state in which the upper fixed unit 10A and the lower movable unit 10B of the dispensing device 10 are moving downward together, the lower movable unit 10B stops the downward movement when the lower end of the tip 31 (if the tip 31 has been attached) or the lower end of the tip nozzle 8 (if the tip 31 has not been attached) makes contact with a container or an obstacle. In this state, if the upper fixed unit 10A continues the downward movement, a gap between the lower end of the upper fixed unit 10A and the upper end of the lower movable unit 10B decreases. After the upper end of the spring 15 has contacted the syringe fixation member 14, the gap between the lower end of the upper fixed unit 10A and the upper end of the lower movable unit 10B decreases further, with the spring 15 being gradually compressed by the driving force moving the upper fixed unit 10A downward.

As above, in this embodiment, the lower movable unit 10B is connected to the upper fixed unit 10A while also being relatively movable with respect to the upper fixed unit 10A. Further, the interior space of the syringe 4 attached to the upper fixed unit 10A and the interior space of the tip nozzle attached to the lower movable unit 10B are connected with each other by the connection tube 1 having flexibility.

Among the components of the upper fixed unit 10A, the driving source 6, the converter 7, the syringe base 12, the plunger 13 and the syringe fixation member 14 are made of metal, whereas the syringe 4 is made of resin. Meanwhile, the tip holding part 5, the connection rod 3 and the spring 15 as the components of the lower movable unit 10B are made of metal. Since the tip holding part 5 is smaller than each component of the upper fixed unit 10A, the weight of the lower movable unit 10B is as light as approximately 1/20 of that of the upper fixed unit 10A.

Therefore, the lower movable unit 10B can stop its movement even when the lower end of the tip 31 makes slight contact with a container or an obstacle. Further, since there is the gap between the syringe fixation member 14 and the upper end of the spring 15, the upper fixed unit 10A is moved quickly even by weak downward driving force until the syringe fixation member 14 contacts the upper end of the spring 15. Furthermore, when the tip 31 is attached to the tip nozzle 8 by press fitting, the spring 15 is compressed between the syringe fixation member 14 and the tip holding part 5 and the biasing force of the spring 15 in this phase serves as the press fitting load on the tip 31. Since the biasing force of the spring 15 can be kept at a constant level, the press fitting load can easily be adjusted and set at an intended value (e.g., 3 kgf).

Incidentally, the connection rod 3 may also be fixed to the syringe fixation member 14 to be slidable with respect to the tip holding part 5.

The photo interrupters 9U and 9L and a detection plate 11 are provided for detecting the status of the gap between the syringe fixation member 14 and the tip holding part 5. The photo interrupters 9U and 9L are attached to the syringe base 12 at positions apart from each other in the Z-axis direction. As shown in FIG. 4, the photo interrupter 9U includes a light-emitting unit 9a (e.g., light-emitting diode) and a photoreceptor unit 9b (e.g., photodiode) arranged across a gap. The photo interrupter 9L also has a similar configuration.

The detection plate 11, which is attached to the tip holding part 5, moves up and down in the Z direction together with the tip holding part 5. The detection plate 11 moves between the gap between the light-emitting unit and the photoreceptor unit of the photo interrupter 9U and the gap between the light-emitting unit and the photoreceptor unit of the photo interrupter 9L. The detection plate 11 has a notch part 11a and a non-notch part 11b (including two non-notch parts). The photo interrupter 9U remains in its ON state when the non-notch part 11b does not exist in the gap of the photo interrupter 9U. The photo interrupter 9L remains in its ON state when the notch part 11a exists in the gap of the photo interrupter 9L. The photo interrupter 9U remains in its OFF state when the non-notch part 11b exists in the gap of the photo interrupter 9U. The photo interrupter 9L remains in its OFF state when the notch part 11a does not exist in the gap of the photo interrupter 9L.

In the state shown in FIG. 2, the tip holding part 5 is situated at its lowest position due to its own weight. In this state, both the photo interrupters 9U and 9L are ON. When the distance between the tip holding part 5 and the syringe fixation member 14 decreases and the distance between the upper end of the spring 15 and the lower end of the syringe fixation member 14 decreases to 0, the photo interrupter 9L turns OFF. Further, when the spring 15 is compressed to its shortest length and the distance between the tip holding part 5 and the syringe fixation member 14 reaches the minimum, the photo interrupter 9U turns OFF. Therefore, the status of the gap between the syringe fixation member 14 and the tip holding part 5 can be detected from the ON/OFF states of the photo interrupters 9U and 9L.

Thus, detecting means including the photo interrupters 9U and 9L and the detection plate 11 detects the relative movement between the upper fixed unit 10A and the lower movable unit 10B. In the state in which the upper end of the spring 15 contacts the lower end of the upper fixed unit 10A, the detecting means detects that the tip 31 attached to the tip nozzle 8 has contacted another object. In the state in which the spring 15 has been compressed, the detecting means detects that the tip 31 has been attached to the tip nozzle 8

A control unit (CU) 100 outputs a driving/stopping control signal to the Z-axis movement mechanism 55Z and thereby controls the driving/stopping of the stepping motor in the Z-axis movement mechanism 55Z. The control unit 100 controls the driving/stopping of the Z-axis movement mechanism 55Z based on the ON/OFF states of the photo interrupters 9U and 9L.

Figure 5:
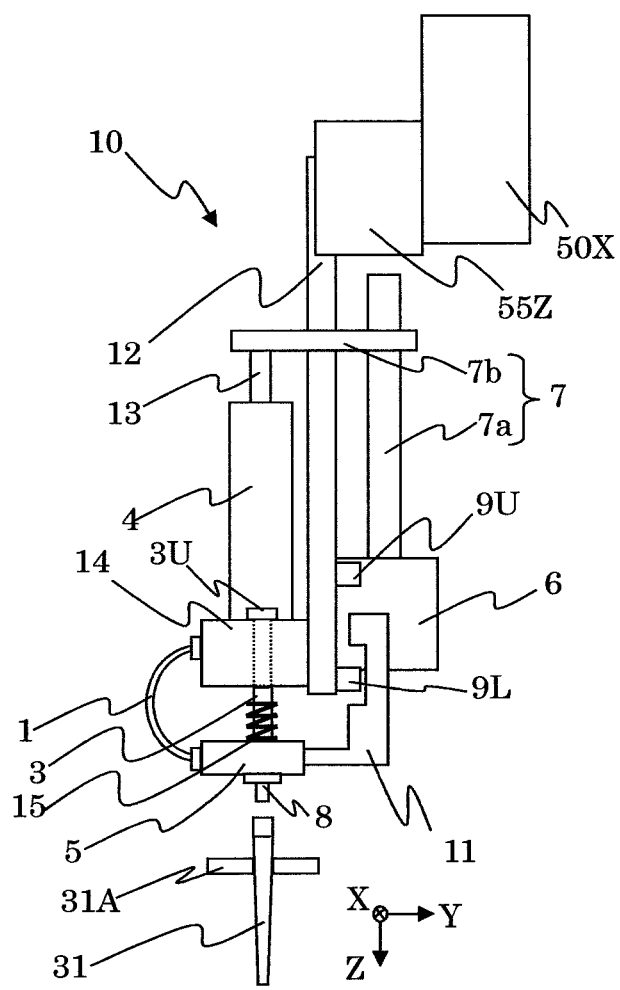
FIG. 5 is a schematic diagram for explaining a tip attaching operation of the dispensing device in accordance with the first embodiment of the present invention.
Figure 6:
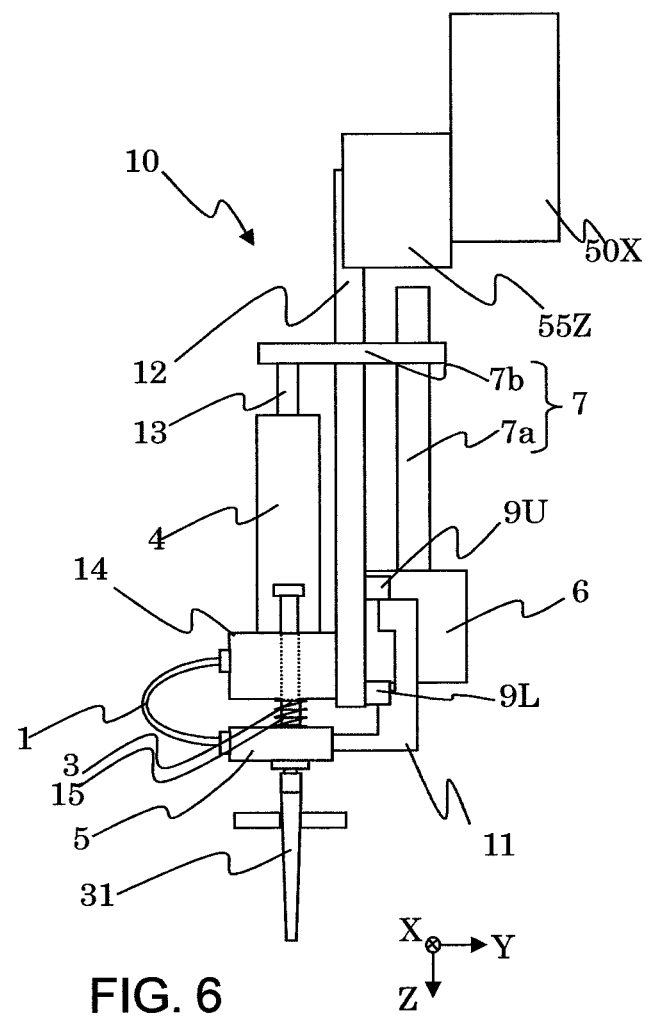
FIG. 6 is a schematic diagram for explaining the tip attaching operation of the dispensing device in accordance with the first embodiment of the present invention.
Figure 7:
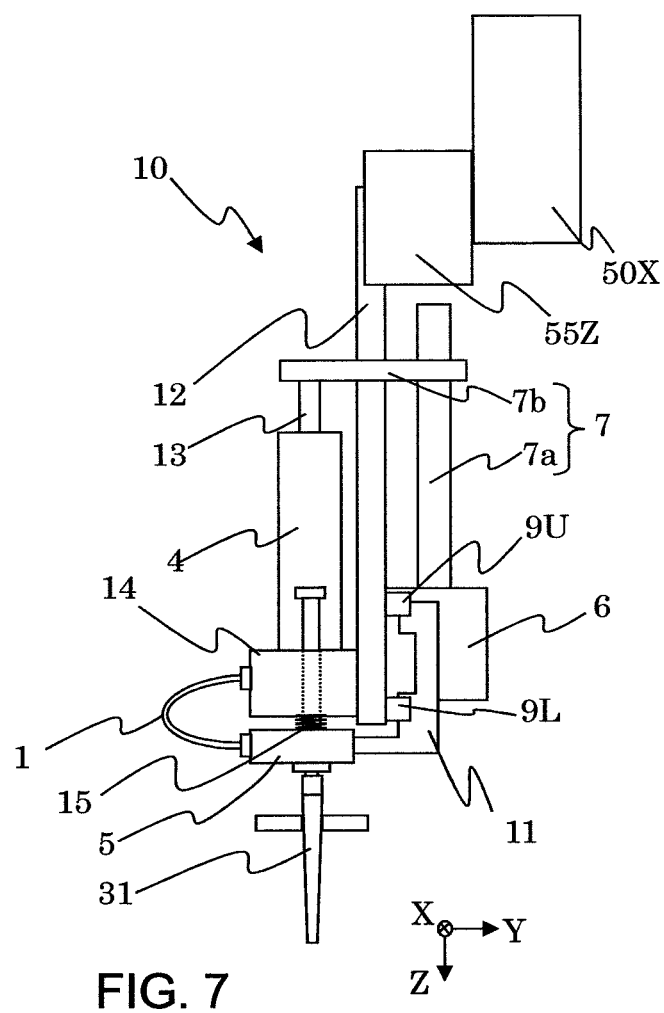
FIG. 7 is a schematic diagram for explaining the tip attaching operation of the dispensing device in accordance with the first embodiment of the present invention.

Next, a tip attaching operation of the dispensing device in accordance with this embodiment will be explained referring to FIGS. 5-7. FIGS. 5-7 are schematic diagrams for explaining the tip attaching operation of the dispensing device in accordance with the first embodiment of the present invention, wherein reference characters identical with those in FIGS. 2-4 represent the same components as in FIGS. 2-4.

As shown in FIG. 5, a tip 31 has been held by the tip holding part 31A. While only one tip 31 is shown in the illustrated example, a plurality of tips 31 are actually held by the tip holding part 31A.

The dispensing device 10 is positioned over one of the tips 31 by the operation of the Y-axis movement mechanism 55Y and the X-axis movement mechanism 55X shown in FIG. 1. In this state, the dispensing device 10 is lowered in the Z-axis direction by operating the Z-axis movement mechanism 55Z.

FIG. 6 shows the state in which the syringe base 12 has moved downward and the tip nozzle 8 has been inserted into the upper opening of the tip 31. When the end of the tip nozzle 8 makes contact with a part of the edge of the upper opening of the tip 31, the descent of the tip holding part 5 (equipped with the tip nozzle 8) stops, whereas the descent of the upper fixed unit 10A (including the syringe fixation member 14) continues. Consequently, the gap between the upper end of the spring 15 and the syringe fixation member 14 decreases. FIG. 6 shows the state in which the gap has decreased to 0. In this state, the non-notch part 11b of the detection plate 11 is situated in the gap of the lower photo interrupter 9L and the output signal of the lower photo interrupter 9L turns OFF. This allows the control unit 100 shown in FIG. 2 to detect that the end of the tip nozzle 8 has contacted the tip 31 (jamming detection).

The tip 31 has not been held by the tip nozzle 8 yet in the state of FIG. 6, and thus the syringe fixation member 14 continues descending due to the operation of the Z-axis movement mechanism 55Z.

Consequently, the spring 15 is compressed between the tip holding part 5 and the syringe fixation member 14 as shown in FIG. 7. By a prescribed amount of biasing force (appropriate inserting force) generated by the compression of the spring 15, the end of the tip nozzle 8 is pressed into the upper opening (inner wall) of the tip 31.

FIG. 7 shows the state in which the spring 15 has been compressed to its minimum length. In this state, the non-notch part 11b of the detection plate 11 is situated in the gap of the upper photo interrupter 9U and the output signal of the upper photo interrupter 9U turns OFF. This allows the control unit 100 shown in FIG. 2 to detect that the tip 31 has been pressed into the end of the tip nozzle 8, that is, the tip has been attached.

By the above operation, the detecting means including the detection plate 11 and the photo interrupters 9 is capable of detecting the relative movement between the upper fixed unit 10A and the lower movable unit 10B. In this case, the photo interrupter 9L detects that the end of the tip nozzle 8 has contacted the tip 31. The upper photo interrupter 9U detects that the tip 31 has been attached to the tip nozzle 8.

Figure 8:
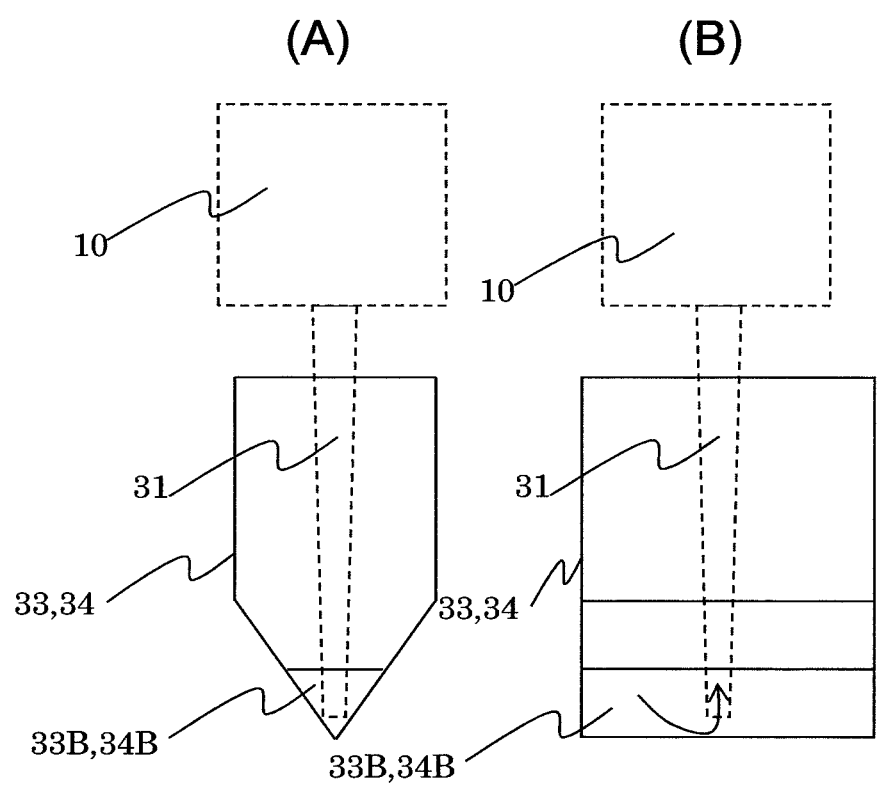
FIG. 8 is schematic diagrams for explaining a liquid suction/discharge operation of the dispensing device in accordance with the first embodiment of the present invention.
Figure 9:
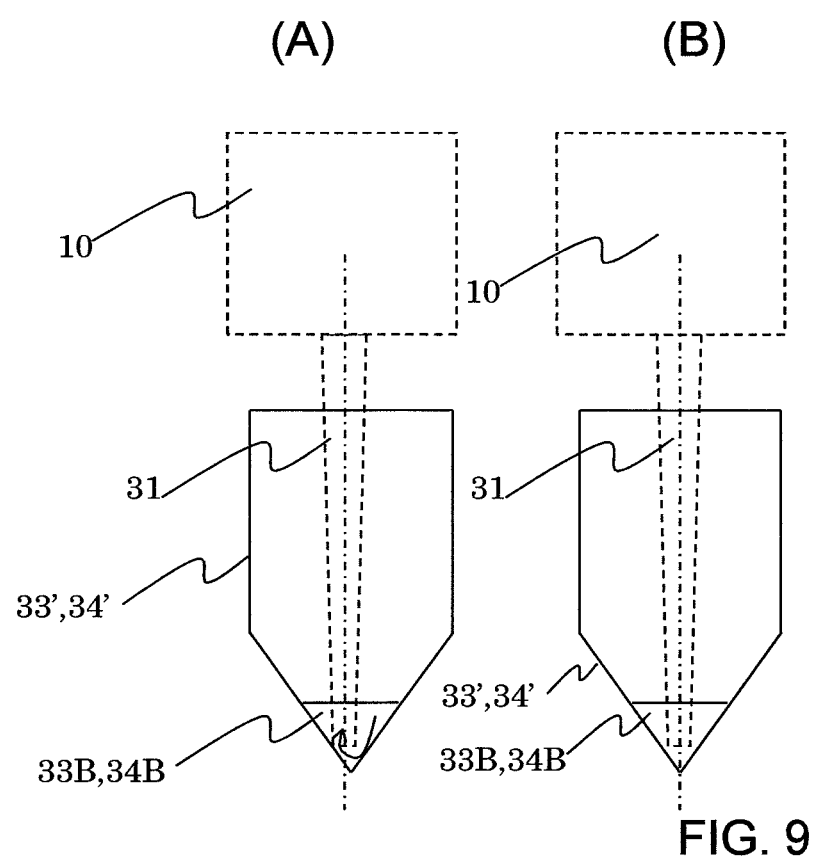
FIG. 9 is schematic diagrams for explaining the liquid suction/discharge operation of the dispensing device in accordance with the first embodiment of the present invention.

Next, a liquid suction/discharge operation of the dispensing device in accordance with this embodiment will be explained referring to FIGS. 2, 8 and 9. FIGS. 8 and 9 are schematic diagrams for explaining the liquid suction/discharge operation of the dispensing device in accordance with the first embodiment of the present invention.

Referring to FIG. 2, the control unit 100 outputs a rotation control signal to the driving source 6 and thereby drives and rotates the stepping motor, etc. of the driving source 6. By the driving in one direction, the plunger 13 moves upward in the Z-axis direction and generates pressure in the space inside the syringe 4. The generated pressure is transmitted through the connected space inside the syringe 4, the syringe fixation member 14, the connection tube 1, the tip holding part 5 and the tip nozzle 8, by which liquid is sucked in through the end of the tip 31. When the driving source 6 rotates in the reverse direction, the plunger 13 moves downward in the Z-axis direction, by which the liquid sucked into the tip 31 is discharged.

Incidentally, since the connection tube 1 is bendable, the pressure caused by the up-and-down movement of the plunger can be reliably transmitted to the tip 31 even when the tip holding part 5 is in contact with another object (foreign object).

FIG. 8 shows the state in which the tip 31 of the dispensing device 10 has been inserted into a reagent container 33 or sample container 34. The container (33, 34) has a V-shaped bottom as shown in FIG. 8 (A) to reduce the amount of liquid that can not be sucked in and remains in the container. FIG. 8 (B) is a right side view of FIG. 8(A).

When the dispensing device 10 is lowered in the Z-axis direction by controlling the Z-axis movement mechanism 55Z shown in FIG. 2, the end of the tip 31 contacts the bottom of the container (33, 34). Upon the contact, the descent of the tip holding part 5 (equipped with the tip tip 31) stops, whereas the descent of the upper fixed unit (including the syringe fixation member 14) continues. Consequently, the gap between the upper end of the spring 15 and the syringe fixation member 14 decreases. When the gap decreases to 0, the output signal of the photo interrupter 9L turns OFF. This allows the control unit 100 to detect that the tip 31 has contacted the bottom of the container 33 or 34 (jamming detection).

Upon the detection of the contact of the tip 31 with the bottom of the container (33, 34), the control unit 100 outputs the rotation control signal to the driving source 6 and thereby drives and rotates the stepping motor, etc. of the driving source 6. The plunger 13 moves upward in the Z-axis direction and generates pressure in the space inside the syringe 4. Due to the generated pressure, the liquid (reagent solution 33B, sample solution 34B) inside the container (33, 34) is sucked in through the end of the tip 31.

This jamming detection function makes it possible to suck in liquid while pressing the tip end (end of the tip 31) of the dispensing device against the bottom of the container containing the liquid (reagent, sample). Therefore, the liquid can be sucked in efficiently even when the amount of the liquid existing in the container is small.

When the dispensing device 10 is moved downward and the end of the tip 31 makes contact with the bottom of the container (33, 34), the deformation of the tip 31 and the container, which are relatively soft (made of polypropylene as plastic having high chemical resistance, for example), is large with respect to the load. In that respect, since the tip holding part 5 can be designed lightweight and the deformation of the tip and the container upon contact can be reduced in this embodiment, an intended amount of liquid can be sucked in correctly while securing a flow channel around the opening at the tip end by the deformation of the tip and the container.

FIG. 9 shows the shape of another container (33', 34'). The container (33', 34') has a conical mortar-like bottom shape. As shown in FIG. 9(A), the flow channel can be secured by performing the sucking operation with the central axes of the tip 31 and the container (33', 34') shifted from each other. The bottom shape of the container is not restricted to the conical mortar-like shape; a container with a round bottom shape may also be used. Incidentally, FIG. 9(B) is a right side view of FIG. 9(A).

From the viewpoint of sucking/discharging a correct amount of liquid by use of the syringe system employing air as the pressure medium, the volume (capacity) of the connected space from the inside of the syringe 4 to the tip 31 is desired to be as smaller as possible compared to the intended amount of the sucked/discharged liquid.

In that respect, the syringe 4 and the tip 31 can be arranged close to each other in this embodiment since the syringe 4 is fixed to the syringe fixation member 14, the tip 31 is attached to the tip holding part 5, the distance between the syringe fixation member 14 and the tip holding part 5 can be as short as approximately the total length of the spring 15. Therefore, the volume (capacity) of the channel inside the connection tube 1 connecting the syringe fixation member 14 and the tip holding part 5 can be set small and high dispensing accuracy can be realized.

Incidentally, while metal such as aluminum can be used as the material of the tip holding part 5, lightweight material such as plastic can also be used in place of metal. The weight of the lower movable unit 10B can be reduced further by use of the lightweight material.

While air is used as the pressure-transmitting fluid in the above example, the dispensing device of this embodiment is applicable also to cases where liquid is used as the pressure-transmitting fluid.

By designing the tip holding part 5 (movable part) lightweight as above, the sensitivity of the jamming detection can be increased, as well as reducing the impact caused by collision.

Further, by placing the spring 15 in its natural length (with its lower end contacting the tip holding part 5 and its upper end not contacting the syringe fixation member 14) as shown in FIG. 2, the distance of displacement until the upper end of the spring 15 contacts the syringe fixation member 14 can be used as displacement for the jamming detection. In the above displacement interval, only the depressing force caused by the weight of the tip holding part 5 is applied to the tip 31. Thus, both the impact on the foreign object and the impact on the dispensing device upon collision can be reduced. Since the occurrence of even a slight load can be detected, high detection accuracy of the jamming detection function can be achieved.

While the connection rod and the spring are used as the mechanism for moving the tip holding part 5 relative to the syringe base 12, a sliding mechanism such as a linear slider can also be used.

While the spring is used for generating the biasing force in the direction obstructing the approximation of the tip holding part 5 to the syringe base 12, other elastic materials such as rubber can also be used.

While the tip holding part 5 is arranged directly under the syringe 4 so that the major axis direction of the tip 31 coincides with that of the syringe 4, the relative positional relationship between the tip holding part 5 and the syringe base 12 equipped with the syringe 4 is not restricted to this example. For example, the syringe base 12 may also be arranged so as to orient the major axis of the syringe 4 in a horizontal direction and so as to be orthogonal to the axis of the tip holding part 5 arranged to orient the major axis of the tip 31 in the vertical direction.

While the dispensing device is designed so that the tip is detachable, the tip and the tip holding part 5 may also be fixed or integrated.

As described above, according to this embodiment, the inside of the syringe 4 and a hollow part of the tip holding part 5 are connected with each other by an elastic hollow-body member (connection tube 1). Thus, the pressure caused by the up-and-down movement of the plunger 13 of the syringe 4 can be transmitted to the end of the tip 31 and the dispensing function can be realized.

Further, since the driving source (e.g., stepping motor) and the mechanism for converting the driving force (e.g., ball screw) are fixed on the syringe base 12 equipped with the syringe 4, the weight of the tip holding part 5 as the movable part can be reduced and a greater upward displacement of the tip holding part 5 with respect to a slighter load can be realized. Since even a slight load can be detected, high detection accuracy for the contact of the tip holding part 5 can be achieved. Furthermore, since the clearance against the deforming load on the tip and the mechanism can also be set large, deterioration in the dispensing performance and malfunction of the mechanism caused by the deformation can be prevented.

Figure 10:
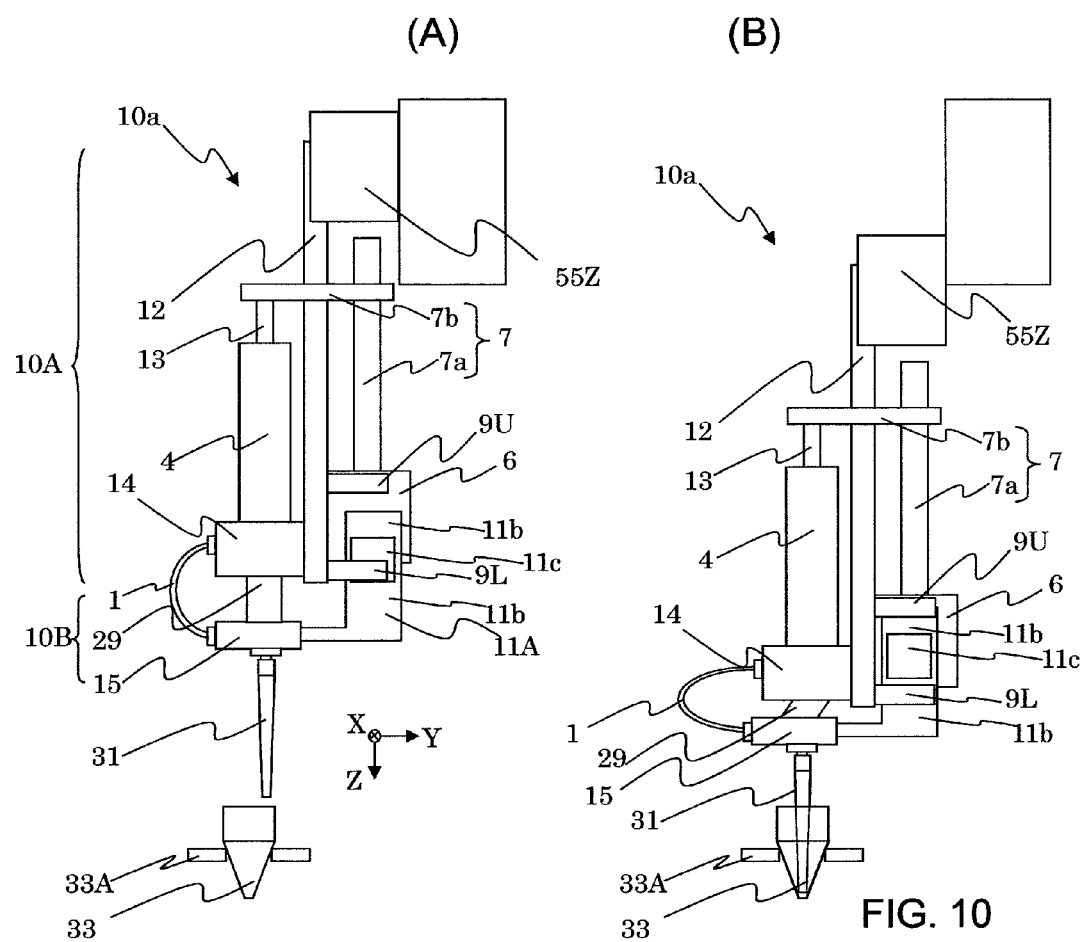
FIG. 10 is front views showing the configuration of a dispensing device in accordance with a second embodiment of the present invention.
Figure 11:
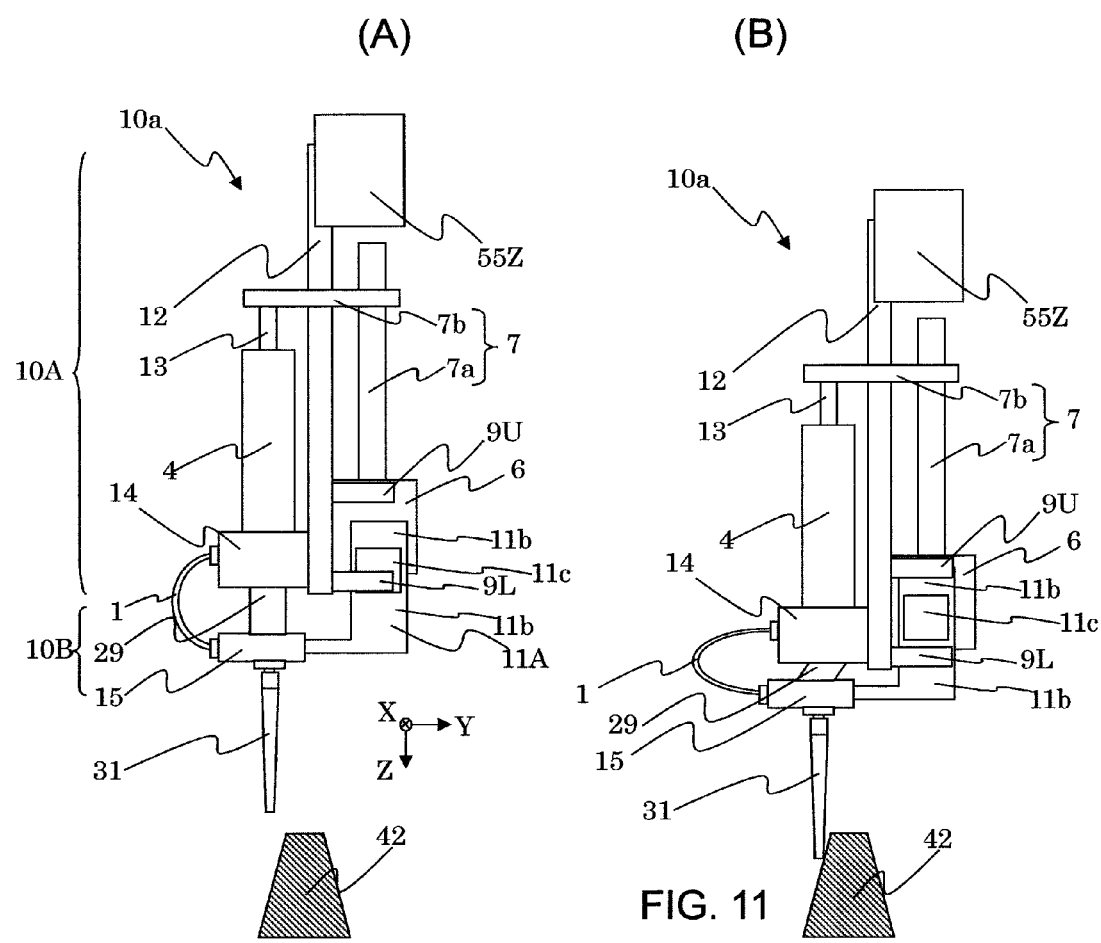
FIG. 11 is front views showing the configuration of the dispensing device in accordance with the second embodiment of the present invention.

Next, the configuration and operation of a dispensing device in accordance with a second embodiment of the present invention will be described with reference to FIGS. 10 and 11. The overall configuration of an automatic analyzer equipped with the dispensing device of this embodiment is as shown in FIG. 1. FIGS. 10 and 11 are front views showing the configuration of the dispensing device in accordance with the second embodiment of the present invention, wherein reference characters identical with those in FIG. 2 represent the same components as in FIG. 2.

In the dispensing device 10a shown in FIG. 10, the basic configuration of the upper fixed unit 10A and the lower movable unit 10B is similar to that shown in FIG. 2. Specifically, the lower movable unit 10B is connected to the upper fixed unit 10A while also being relatively movable with respect to the upper fixed unit 10A. The interior space of the syringe 4 attached to the upper fixed unit 10A and the interior space of the tip nozzle attached to the lower movable unit 10B are connected with each other by the connection tube 1 having flexibility.

In this embodiment, the configuration of the part connecting the upper fixed unit 10A and the lower movable unit 10B is different.

The syringe fixation member 14 of the upper fixed unit 10A and the tip holding part 5 of the lower movable unit 10B are connected with each other by an elastic member 29. For example, relatively soft rubber material such as silicone rubber is used as the elastic member 29. The elastic member 29 allows for displacement of the tip holding part 5 relative to the syringe fixation member 14 both in the Z-axis direction and in the Y-axis direction. While displacement in the X-axis direction is also possible, this explanation will be given assuming that the jamming detection is executed using a detection plate 11A and photo interrupters 9U' and 9L' for detecting the displacement in the Z-axis direction and the Y-axis direction.

As shown in FIG. 10, a reagent container 33 has been held by the reagent container holding part 33A. While only one reagent container 33 is shown in the illustrated example, a plurality of reagent containers 33 are actually held by the reagent container holding part 33A. Incidentally, the following explanation holds also for cases where not a reagent container but a sample container is used.

FIG. 10(A) shows a state in which the dispensing device 10a has moved downward in the dispensing operation. In the illustrated state, the central axis of the tip 31 has shifted rightward in FIG. 10(A) with respect to the central axis of the reagent container 33.

From the state shown in FIG. 10(A), the dispensing device 10a is lowered by the Z-axis movement mechanism 55Z. In the state shown in FIG. 10(A), the output of the photo interrupter 9L is ON since an opening part 11c of the detection plate 11A exists in the gap of the photo interrupter 9L. The output of the photo interrupter 9U is also ON since the detection plate 11A does not exist in the gap of the photo interrupter 9U.

When the dispensing device 10a is moved downward, the end of the tip 31 makes contact with an inclined inner surface of the reagent container 33. Since the lower movable unit 10B receives leftward force in FIG. 10(A) due to the contact, the elastic member 29 deforms and moves leftward. Meanwhile, the upper fixed unit 10A continues the downward movement. Consequently, a non-opening part 11b of the detection plate 11A comes to the gap of the photo interrupter 9L and the output of the photo interrupter 9L turns OFF, by which the jamming can be detected. At this point, the upper photo interrupter 9U remains ON. The end of the tip 31 is situated at the lowest part of the reagent container 33, which makes it possible to suck in the reagent remaining at the bottom of the reagent container 33.

In the tip attaching operation in which strong force is applied to the tip 31, the elastic member 29 deforms until both the photo interrupters 9U and 9L become OFF, by which the attachment of the tip can be detected.

FIG. 11 shows a state in which the X rail 50X is being driven in the Y-axis direction by the Y-axis movement mechanism 55Y shown in FIG. 1 after the dispensing device 10a has been moved downward.

It is assumed that an obstacle 42 exists under the dispensing device 10a when the dispensing device 10a is lowered by the Z-axis movement mechanism 55Z from the state shown in FIG. 11(A). In the state shown in FIG. 11(A), the output of the photo interrupter 9L is ON since the opening part 11c of the detection plate 11A exists in the gap of the photo interrupter 9L. The output of the photo interrupter 9U is also ON since the detection plate 11A does not exist in the gap of the photo interrupter 9U.

When the dispensing device 10a is moved in the Y-axis direction (rightward in FIG. 11 as shown in FIG. 11(B)) after being moved downward, the end of the tip 31 makes contact with the obstacle 42. Due to the contact, the lower movable unit 10B stops moving and the upper fixed unit 10A continues moving in the Y-axis direction, by which the lower movable unit 10B is moved upward. Consequently, the non-opening part 11b of the detection plate 11A comes to the gap of the photo interrupter 9L and the output of the photo interrupter 9L turns OFF, by which the jamming can be detected.

With this configuration, the impact caused by the collision with the obstacle can be reduced in the vertical and horizontal directions, while increasing the jamming detection sensitivity by employing the lightweight tip holding part 5. Further, by making the tip actively contact the liquid container, high dispensing accuracy can be secured and the scattering of the liquid can be prevented.

By the above operation, the detecting means including the detection plate 11A and the photo interrupters 9 is capable of detecting the relative movement between the upper fixed unit 10A and the lower movable unit 10B. In this case, the photo interrupter 9L detects that the tip 31 attached to the tip nozzle 8 has contacted another object (container, obstacle, etc.). The upper photo interrupter 9U detects that the tip 31 has been attached to the tip nozzle 8.

As described above, according to this embodiment, the inside of the syringe 4 and the hollow part of the tip holding part 5 are connected with each other by an elastic hollow-body member (connection tube 1). Thus, the pressure caused by the up-and-down movement of the plunger 13 of the syringe 4 can be transmitted to the end of the tip 31 and the dispensing function can be realized.

Further, since the driving source (e.g., stepping motor) and the mechanism for converting the driving force (e.g., ball screw) are fixed on the syringe base 12 equipped with the syringe 4, the weight of the tip holding part 5 as the movable part can be reduced and a greater upward displacement of the tip holding part 5 with respect to a slighter load can be realized. Since even a slight load can be detected, high detection accuracy for the contact of the tip holding part 5 can be achieved. Furthermore, since the clearance against the deforming load on the tip and the mechanism can also be set large, deterioration in the dispensing performance and malfunction of the mechanism caused by the deformation can be prevented.

Figure 12:
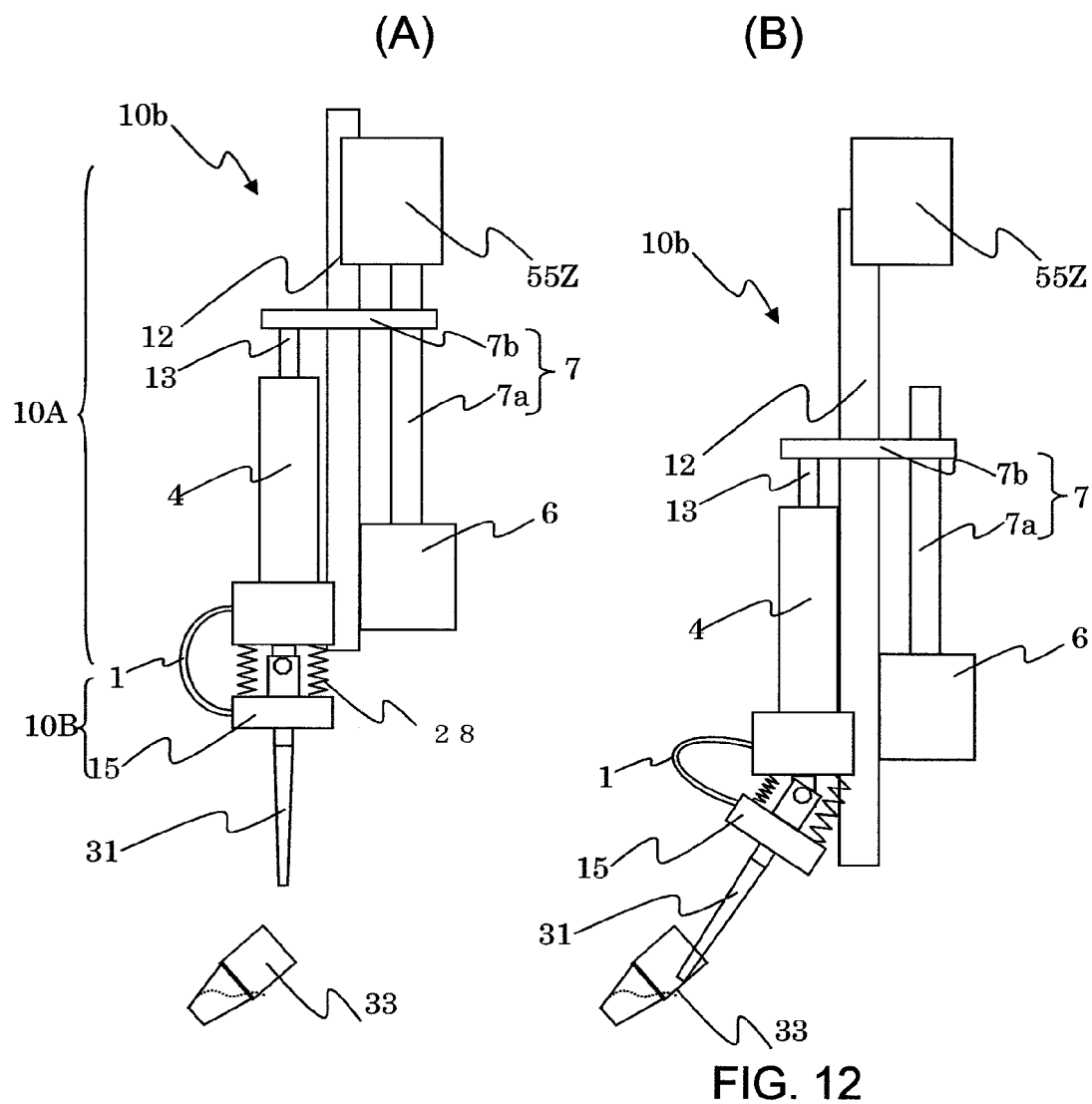
FIG. 12 is front views showing the configuration of a dispensing device in accordance with a third embodiment of the present invention.
Figure 13:
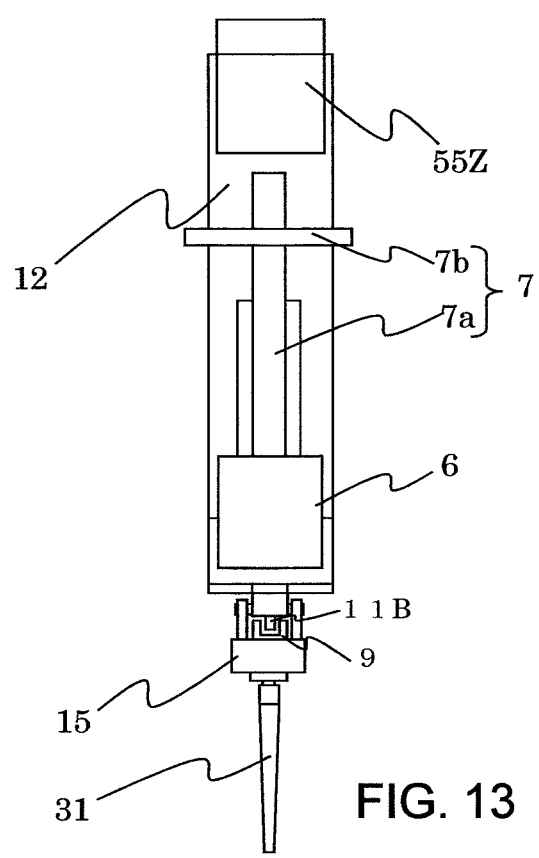
FIG. 13 is a right side view of FIG. 12.

Next, the configuration and operation of a dispensing device in accordance with a third embodiment of the present invention will be described with reference to FIGS. 12 and 13. The overall configuration of an automatic analyzer equipped with the dispensing device of this embodiment is as shown in FIG. 1. FIG. 12 is a front view showing the configuration of the dispensing device in accordance with the third embodiment of the present invention, wherein reference characters identical with those in FIG. 2 represent the same components as in FIG. 2. FIG. 13 is a right side view of FIG. 12.

In the dispensing device 10b shown in FIG. 12, the basic configuration of the upper fixed unit 10A and the lower movable unit 10B is similar to that shown in FIG. 2. Specifically, the lower movable unit 10B is connected to the upper fixed unit 10A while also being relatively movable with respect to the upper fixed unit 10A. The interior space of the syringe 4 attached to the upper fixed unit 10A and the interior space of the tip nozzle attached to the lower movable unit 10B are connected with each other by the connection tube 1 having flexibility.

In this embodiment, the configuration of the part connecting the upper fixed unit 10A and the lower movable unit 10B is different.

The syringe fixation member 14 of the upper fixed unit 10A and the tip holding part 5 of the lower movable unit 10B are connected with each other by a hinge 23 and two springs 28. The hinge 23 is capable of rotating around its rotation center and thereby changing the lean of the lower movable unit 10B.

For example, when the dispensing device 10b descends in the state shown in FIG. 12(A) and the tip 31 makes contact with the inner wall of the liquid container 33 placed obliquely, the lower movable unit 10B rotates around the hinge 23 and leans along the inner wall of the container 33 as shown in FIG. 12(B), by which the tip holding part 5 is set at an appropriate angle (hereinafter referred to as "edging"). As above, the angle of the edging can be controlled by the contact of the tip 31 with the liquid container or the like.

The tip can be inserted into an obliquely placed container 33 (e.g., centrifuge) and the contents of the container can be sucked in or liquid can be discharged into the container without scattering the liquid to the outside of the container. Therefore, automation of the dispensing of liquid from a centrifuge can be carried out with ease and reliability.

Incidentally, while the elastic member 28 is employed for the dispensing device and the elastic member 28 sets the static position of the tip holding part 5 in the noncontact state in the example of FIG. 12, it is also possible to leave out the elastic member 28 and let the weight of the tip holding part 5 set the static position.

The jamming detection is executed using a detection plate 11B and a photo interrupter 9 shown in FIG. 13. The detection plate 11B is attached to the lower movable unit 10B, while the photo interrupter 9 is attached to the upper fixed unit 10A. In the state shown in FIG. 12(A), the detection plate 11B has been inserted in the gap of the photo interrupter 9 and thus the photo interrupter 9 is OFF. When the lower movable unit 10B leans to the lean angle shown in FIG. 12(B), the detection plate 11B goes out of the gap of the photo interrupter 9 and the photo interrupter 9 turns ON, by which the jamming can be detected.

By the above operation, the detecting means including the detection plate 11B and the photo interrupter 9 is capable of detecting the relative movement between the upper fixed unit 10A and the lower movable unit 10B. In this case, the photo interrupter 9 detects that the tip 31 attached to the tip nozzle 8 has contacted another object (container, obstacle, etc.) and has been set at a prescribed lean angle (edging).

As described above, according to this embodiment, the inside of the syringe 4 and the hollow part of the tip holding part 5 are connected with each other by an elastic hollow-body member (connection tube 1). Thus, the pressure caused by the up-and-down movement of the plunger 13 of the syringe 4 can be transmitted to the end of the tip 31 and the dispensing function can be realized.

Further, since the driving source (e.g., stepping motor) and the mechanism for converting the driving force (e.g., ball screw) are fixed on the syringe base 12 equipped with the syringe 4, the weight of the tip holding part 5 as the movable part can be reduced and a greater upward displacement of the tip holding part 5 with respect to a slighter load can be realized. Since even a slight load can be detected, high detection accuracy for the contact of the tip holding part 5 can be achieved. Furthermore, since the clearance against the deforming load on the tip and the mechanism can also be set large, deterioration in the dispensing performance and malfunction of the mechanism caused by the deformation can be prevented.

Since a lean angle can be given to the tip by the combination with a centrifuge, the insertion of the tip into an oblique container is facilitated and the suction/discharge of the liquid can be carried out while making the tip end contact the inner wall of the container or avoiding the contact.

By making the tip end contact the inner wall of the container, the liquid discharged from the tip can be prevented from partially adhering to the tip end and remaining without being pipetted into the container. By actively edging (i.e., giving a lean angle to) the tip, the contamination between the tip and the liquid/container can be avoided.

By inserting the tip end into the inside of the container, the liquid is injected in a wide range from the tip end when the liquid discharging speed is high, by which problems such as deterioration in the dispensing accuracy and scattering of the liquid can be avoided.

Figure 14:
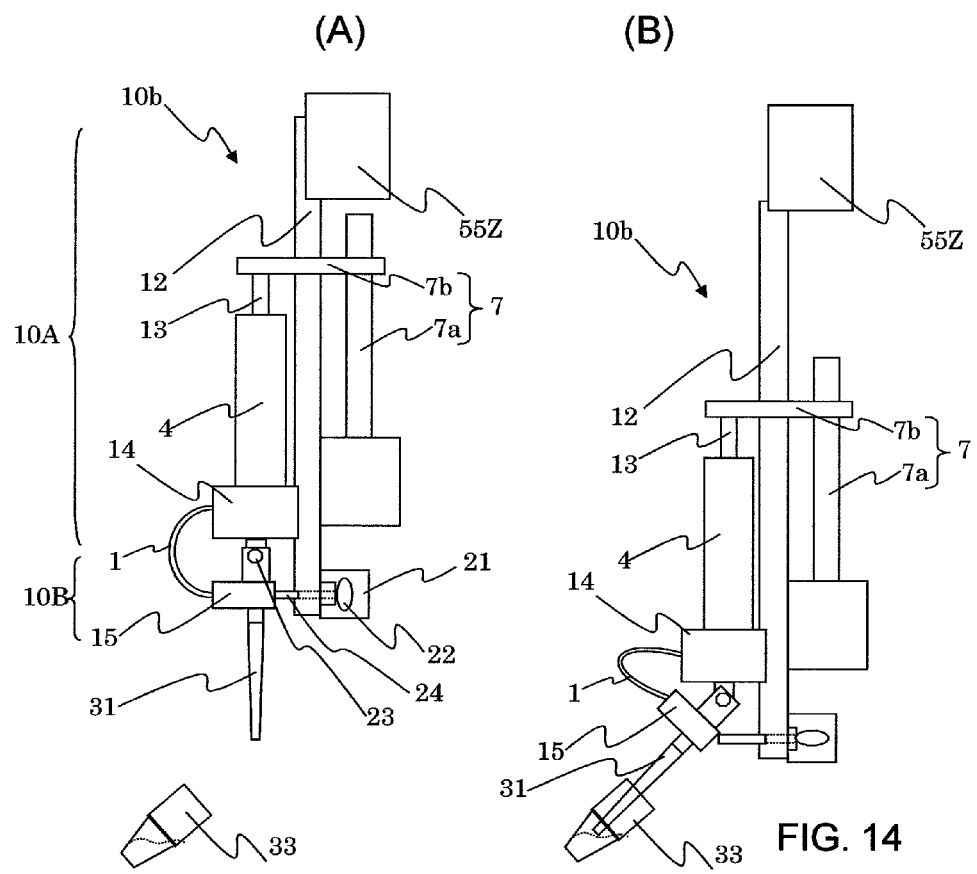
FIG. 14 is front views showing the configuration of a dispensing device in accordance with a fourth embodiment of the present invention.

Next, the configuration and operation of a dispensing device in accordance with a fourth embodiment of the present invention will be described with reference to FIG. 14. The overall configuration of an automatic analyzer equipped with the dispensing device of this embodiment is as shown in FIG. 1. FIG. 14 is front views showing the configuration of the dispensing device in accordance with the fourth embodiment of the present invention, wherein reference characters identical with those in FIG. 2 represent the same components as in FIG. 2.

In the dispensing device 10c shown in FIG. 14, the basic configuration of the upper fixed unit 10A and the lower movable unit 10B is similar to that shown in FIG. 2. In this embodiment, the configuration of the part connecting the upper fixed unit 10A and the lower movable unit 10B is different.

The syringe fixation member 14 of the upper fixed unit 10A and the tip holding part 5 of the lower movable unit 10B are connected with each other by a hinge 23. The hinge 23 is capable of rotating around its rotation center and thereby changing the lean of the lower movable unit 10B. The dispensing device is further equipped with a cam 22 which is rotated by a motor 21. According to the rotation of the cam 22, a push rod 24 in contact with the cam surface pushes out the tip holding part 5, by which the tip holding part 5 is leaned around the hinge 23 and the edging of the tip holding part 5 is conducted. As above, the angle of the edging can be controlled when the tip 31 contacts with the liquid container or the like.

The dispensing device of this embodiment is similarly equipped with the detection plate 11B and the photo interrupter 9 shown in FIG. 13 (although not shown in FIG. 14), with which the jamming detection is possible. The jamming detection can also be executed based on the rotation angle of the cam 22 rotated by the motor 21.

As described above, according to this embodiment, the inside of the syringe 4 and the hollow part of the tip holding part 5 are connected with each other by an elastic hollow-body member (connection tube 1). Thus, the pressure caused by the up-and-down movement of the plunger 13 of the syringe 4 can be transmitted to the end of the tip 31 and the dispensing function can be realized.

Further, since the driving source (e.g., stepping motor) and the mechanism for converting the driving force (e.g., ball screw) are fixed on the syringe base 12 equipped with the syringe 4, the weight of the tip holding part 5 as the movable part can be reduced and a greater upward displacement of the tip holding part 5 with respect to a slighter load can be realized. Since even a slight load can be detected, high detection accuracy for the contact of the tip holding part 5 can be achieved. Furthermore, since the clearance against the deforming load on the tip and the mechanism can also be set large, deterioration in the dispensing performance and malfunction of the mechanism caused by the deformation can be prevented.

Since an angle can be given to the tip by the combination with a centrifuge, the insertion of the tip into an oblique container is facilitated and the suction/discharge of the liquid can be carried out while making the tip end contact the inner wall of the container or avoiding the contact.

By making the tip end contact the inner wall of the container, the liquid discharged from the tip can be prevented from partially adhering to the tip end and remaining without being pipetted into the container. By actively edging the tip, the contamination between the tip and the liquid/container can be avoided.

By inserting the tip end into the inside of the container, the liquid is injected in a wide range from the tip end when the liquid discharging speed is high, by which problems such as deterioration in the dispensing accuracy and scattering of the liquid can be avoided.

Figure 15:
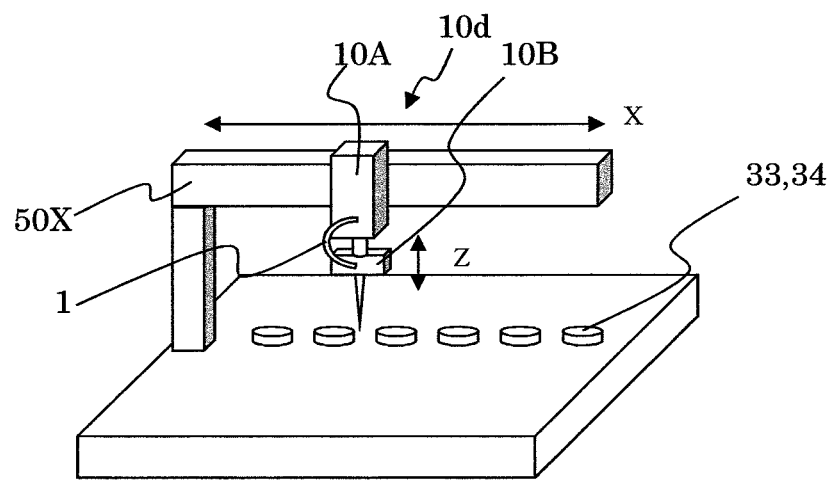
FIG. 15 is a perspective view of a modification of the automatic analyzer shown in FIG. 1.
Figure 16:
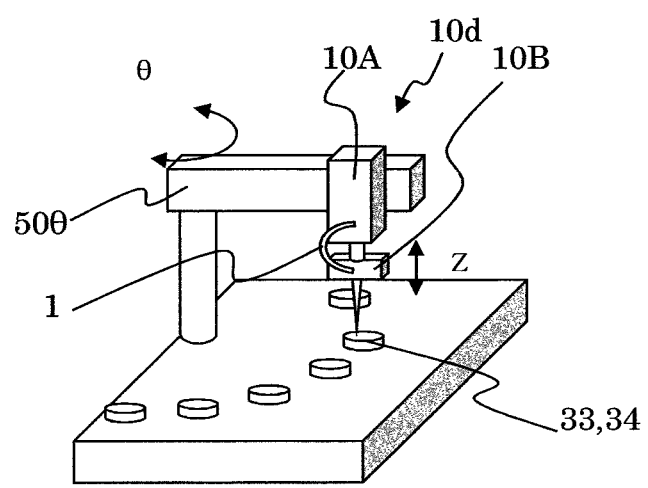
FIG. 16 is a perspective view of a modification of the automatic analyzer shown in FIG. 1.
Figure 17:
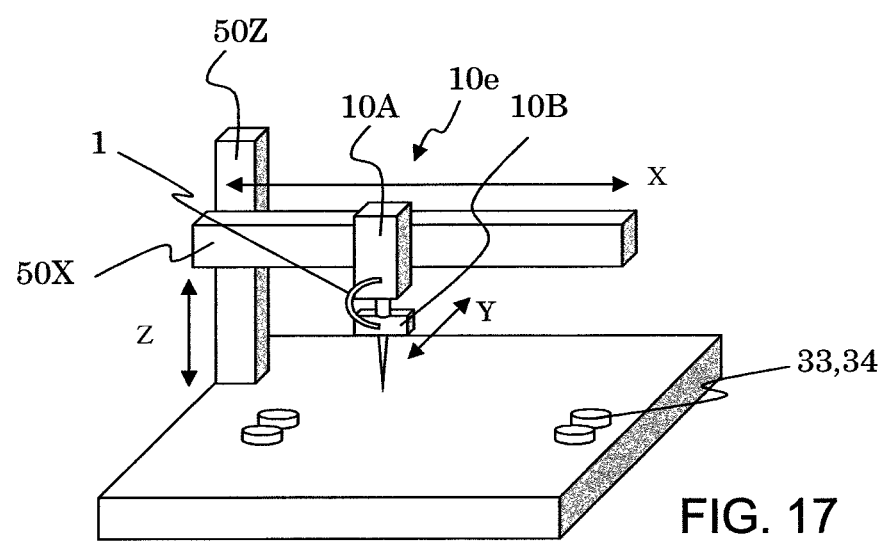
FIG. 17 is a perspective view of a modification of the automatic analyzer shown in FIG. 1.

Next, modifications of the automatic analyzer shown in FIG. 1 will be described with reference to FIGS. 15-17. FIGS. 15-17 are perspective views of the modifications of the automatic analyzer shown in FIG. 1.

In an example shown in FIG. 15, an upper fixed unit 10A including a syringe is attached to an X arm 50X and can be driven in the X direction shown in FIG. 17. A lower movable unit 10B includes a tip holding part. The tip holding part is connected with the inside of the syringe of the upper fixed unit 10A by a connection tube 1. The upper fixed unit 10A includes a mechanism for driving the lower movable unit 10B in the Z direction. The dispensing device 10d comprising the upper fixed unit 10A and the lower movable unit 10B is movable along the X arm 50X over liquid containers (reagent containers 33, sample containers 34) aligned in the X direction.

In an example shown in FIG. 16, the dispensing device 10d shown in FIG. 5 is supported by a θ arm 50θ. The θ arm 50θ is capable of rotating in the θ direction shown in FIG. 16. The upper fixed unit 10A includes a mechanism for driving the lower movable unit 10B in the Z direction.

In an example shown in FIG. 17, a dispensing device 10e can be driven in the X direction with respect to an X arm 50X. The X arm 50X can be driven in the Z direction with respect to a Z arm 50Z. The dispensing device 10e comprises an upper fixed unit 10A and a lower movable unit 10B. The lower movable unit 10B can be driven in the Y direction with respect to the upper fixed unit 10A. The driving in the Y direction is performed by a linear motor, etc. installed in the upper fixed unit 10A.

In cases where liquid containers (reagent containers 33, sample containers 34) are arranged to be apart in the X direction and close in the Y direction, the movement in the X direction is performed by the X arm capable of high-speed driving and the movement in the Y direction is performed by the moving mechanism installed in the upper fixed unit 10A.

Since the movement in the Y direction (light load and short distance compared to the movement in the X direction) can be implemented by a relatively small-scale moving mechanism, the total weight of the dispensing device can be reduced. Further, since the resolution of the driving in the Y direction can be made finer, the density of the arrangement of the liquid containers in the Y direction can be increased and the dispensing device can be downsized.

As above, also in the embodiments shown in FIGS. 15-17, the lower movable unit 10B is connected to the upper fixed unit 10A while also being relatively movable with respect to the upper fixed unit 10A. The interior space of the syringe 4 attached to the upper fixed unit 10A and the interior space of the tip nozzle attached to the lower movable unit 10B are connected with each other by the connection tube 1 having flexibility.

According to the above configurations, a mechanism that drives only the lower movable unit 10B (including the lightweight tip holding part), instead of driving the whole of the dispensing device in the Z-axis direction, is employed, and thus the mechanism can be designed lightweight. Since the operating time can be shortened by the weight reduction, the time necessary for the dispensing (in a dispensing device) and analysis (in an analyzer) can be shortened.

Figure 18:
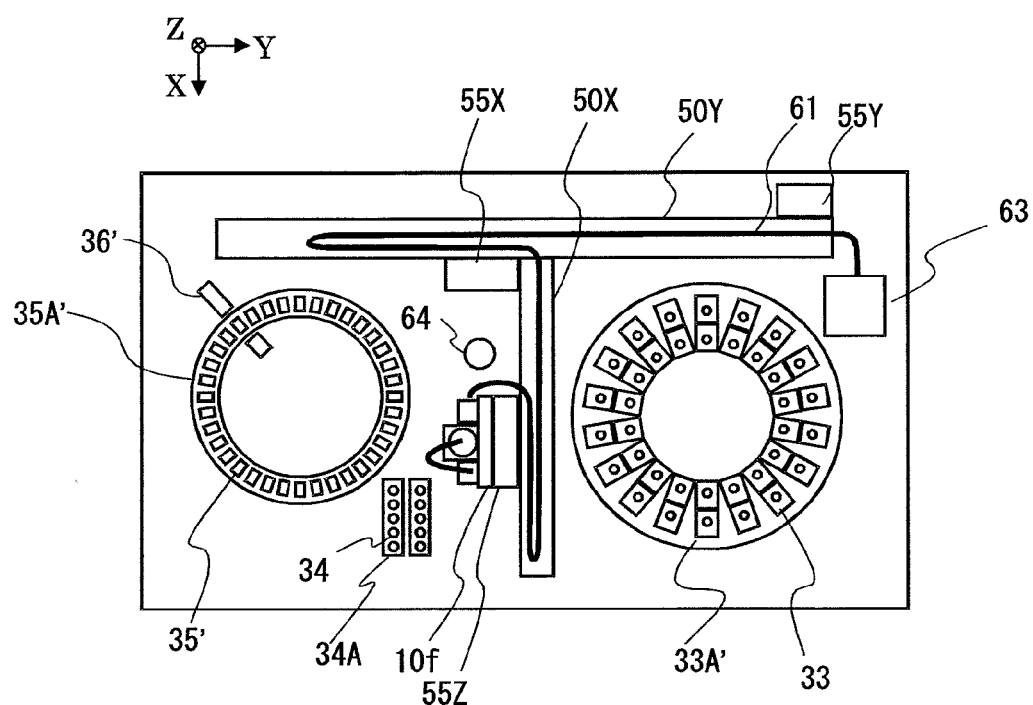
FIG. 18 is a plan view showing the configuration of an automatic analyzer equipped with a dispensing device in accordance with a fifth embodiment of the present invention.
Figure 19:
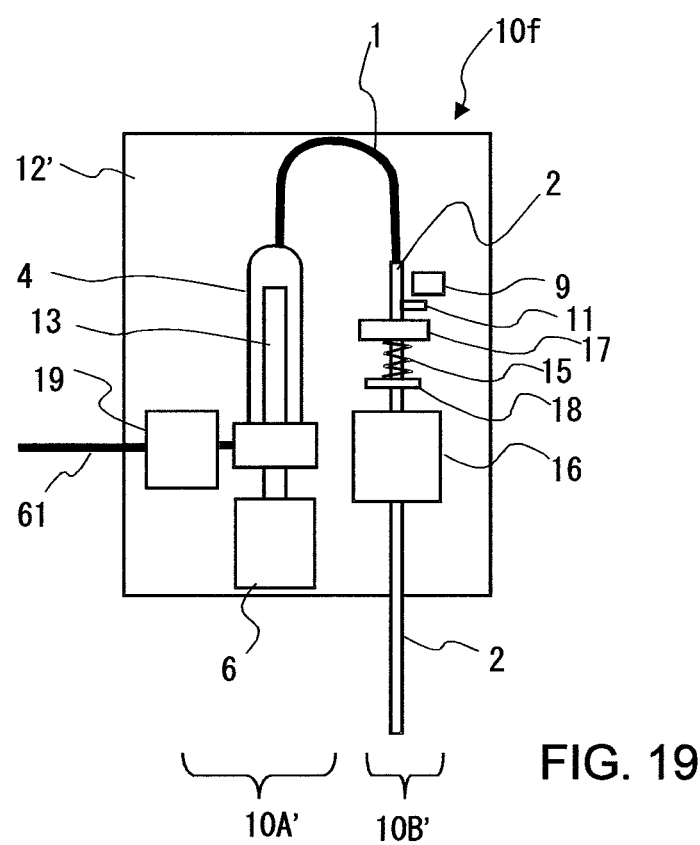
FIG. 19 is a front view showing the configuration of the dispensing device in accordance with the fifth embodiment of the present invention.

Next, the configuration and operation of a dispensing device in accordance with a fifth embodiment of the present invention will be described with reference to FIGS. 18 and 19. First, the configuration and operation of an automatic analyzer equipped with the dispensing device of this embodiment will be explained referring to FIG. 18. The following explanation will be given by taking an automatic analyzer for analyzing blood, etc. as an example of the automatic analyzer. FIG. 18 is a plan view showing the configuration of the automatic analyzer equipped with the dispensing device in accordance with the fifth embodiment of the present invention, wherein reference characters identical with those in FIG. 1 represent the same components as in FIG. 1.

The automatic analyzer explained referring to FIG. 1 uses air as the fluid for transmitting the pressure generated in the syringe. However, the dispensing devices which have been shown in FIG. 2, etc. are characterized in that the dispensing device comprises the upper fixed unit and the lower movable unit, the two units are connected with each other by a connection tube, the connection tube is used as the channel for transmitting the pressure of the fluid, and a flexible tube is used as the connection tube. Therefore, the idea of the dispensing devices shown in FIG. 2, etc. is applicable also to an automatic analyzer for analyzing blood, etc. that uses liquid as the pressure-transmitting fluid.

In the example shown in FIG. 18, reagent containers 33 are mounted on a reagent disk 33A' and reaction containers 35 are mounted on a reaction disk 35A'. A detection unit 36' is placed on the circumference of the reaction disk 35A'. Further, a cleaning liquid pump 63 is connected to the dispensing device 10f by a cleaning liquid tube 61. A cleaning port 64 is placed within the moving range of the dispensing device 10f.

The dispensing device 10f is attached to an X arm 50X to be movable in the X direction by an X-axis movement mechanism 55X. The X arm 50X is attached to a Y rail 50Y to be movable in the Y direction by a Y-axis movement mechanism 55Y. The dispensing device 10f is movable also in the Z direction by a Z-axis movement mechanism 55Z.

As will be explained later referring to FIG. 19, the automatic analyzer for analyzing blood, etc. uses a nozzle for the dispensing of liquid, without using the replaceable tips. Thus, the automatic analyzer is not equipped with the tip, the tip holding part, etc. The basic operation of the other components is similar to that explained referring to FIG. 1.

Next, the configuration and operation of the dispensing device in accordance with this embodiment will be described with reference to FIG. 19. FIG. 19 is a front view showing the configuration of the dispensing device in accordance with the fifth embodiment of the present invention, wherein reference characters identical with those in FIG. 18 represent the same components as in FIG. 18.

The dispensing device 10f comprises a fixed unit 10A' and a movable unit 10B'. A syringe 4 as a component of the fixed unit 10A' and a nozzle 2 as a component of the movable unit 10B' are connected with each other by a connection tube 1 having flexibility. As above, also in this embodiment, the movable unit 10B' is connected to the fixed unit 10A' while also being relatively movable with respect to the fixed unit 10A'. The interior space of the syringe 4 attached to the fixed unit 10A' and the interior space of the nozzle 2 attached to the movable unit 10B' are connected with each other by the connection tube 1 having flexibility.

The left fixed unit 10A' includes a driving source 6 (fixed on a syringe base 12'), the syringe 4 and a valve 19. The driving source 6 moves a plunger 13 to and fro and thereby generates pressure inside the syringe 4. The cleaning liquid is introduced into the inside of the syringe 4 via the cleaning liquid tube 61 and the valve 19 as the pressure-transmitting fluid. A nozzle guide 16, a stopper 17 and a photo interrupter 9 for the jamming detection are fixed on the syringe base 12'.

The right movable unit 10B' includes the nozzle 2, a spring 15, a spring holding part 18 and a detection plate 11. The nozzle 2 is held by the nozzle guide 16 to be movable to and fro (up and down). The connection tube 1 is connected to the upper end of the nozzle 2. The spring holding part 18 is attached to the nozzle 2. The spring 15 is arranged between the stopper 17 and the spring holding part 18 to surround the nozzle 2. The detection plate 11 is attached to the upper part of the nozzle 2. A spring having a small spring constant is employed as the spring 15 since the spring 15 is used for the jamming detection. When the nozzle 2 moves upward, the spring holding part 18 also moves upward and compresses the spring 15. In this case, when the detection plate 11 also moving upward is inserted into the gap of the photo interrupter 9, the output of the photo interrupter 9 turns OFF.

By the above operation, the detecting means including the detection plate 11 and the photo interrupter 9 is capable of detecting the relative movement of the movable unit 10B' with respect to the fixed unit 10A'. In this case, the photo interrupter 9 detects that the nozzle 2 has contacted another object (container, obstacle, etc.).

Next, the operation of the analyzer and the dispensing device of this embodiment will be described referring to FIGS. 18 and 19.

The dispensing device 10f is moved to the cleaning port 64. At the cleaning port 64, the nozzle 2 is washed and cleaned by opening the valve 19 and letting the cleaning liquid (supplied from the cleaning liquid pump 63) flow out through the nozzle 2. After the cleaning is finished, the valve 19 is closed.

Subsequently, the dispensing device 10f is moved to a position over a selected sample container 34 and a prescribed amount of sample solution is sucked in by moving the plunger 13 downward by the driving source 6. Then, the dispensing device 10f is moved to a position over one reaction container 35 on the reaction disk 35A', descends until the photo interrupter 9 reacts, and discharges a prescribed amount of the sample solution. Thereafter, the dispensing device 10f is moved to the position of the cleaning port 64 and the nozzle 2 is washed and cleaned by opening the valve 19 and letting the cleaning liquid (supplied from the cleaning liquid pump 63) flow out through the nozzle 2.

Subsequently, the dispensing device 10f is moved to a position over the reagent disk 33A' and sucks in a reagent solution from a selected reagent container 33. Then, the dispensing device 10f is moved to the aforementioned position of the reaction disk 35A' and discharges a prescribed amount of the reagent solution into the reaction container 35. When multiple types of reagents are used, the dispensing of a reagent is executed multiple times.

The reaction disk 35A' periodically repeats rotation and stoppage. Optical detection is conducted when the reaction container 35 (into which the sample and the reagent have been pipetted) passes through the detection unit 36'. From the result of the optical detection, the concentration of a particular ingredient of the sample solution is calculated and outputted.

In this embodiment, the nozzle 2 is washed and cleaned on each execution of the dispensing. Therefore, high-precision analysis, free from contamination by other samples or reagents, can be performed without the need of using the tips. Consequently, low-cost analysis is made possible.

Since each liquid is discharged after the nozzle 2 is lowered until the photo interrupter 9 reacts, the discharging of each liquid can be performed with the end of the nozzle 2 securely contacting the bottom of the reaction container 35. Thus, high-accuracy dispensing is possible.

Since the lightweight nozzle 2 is movable with respect to the dispensing device 10f, the impact when the end of the nozzle 2 contacts the bottom of the reaction container 35 is weak and the damage to the reaction container is light. Effects of deformation/vibration of the reaction disk 35A' on the reaction/detection in other reaction containers can be minimized, which enables high-accuracy analysis.

Since the syringe 4 and the connection tube 1 are filled with liquid having a lower expansion rate than gas and the amount of the discharge from the syringe 4 can be transmitted to the nozzle 2 correctly, the accuracy of the dispensing is high and high-accuracy analysis is possible.

Since the syringe 4 and the nozzle 2 are connected with each other by the connection tube 1 having flexibility, the change in the capacity of the connection tube 1 caused by the change in the position of the nozzle 2 is small. Therefore, high-accuracy analysis can be conducted with high dispensing accuracy.

Since the syringe 4 and the nozzle 2 are connected with each other by the curved connection tube 1, the need of arranging the syringe 4 and the nozzle 2 in a line is eliminated and a compact device can be realized.

Since the syringe 4 and the nozzle 2 are connected with each other by the curved connection tube 1, the outlet of the syringe can be pointed upward. Therefore, bubbles remaining in the syringe can be prevented and high-accuracy analysis can be conducted with high dispensing accuracy.

Since the syringe 4 and the nozzle 2 are mounted on the same movement mechanism, the connection tube is allowed to be short. Therefore, dispersion (inaccuracy) in the dispensing, caused by delay of the fluid or changes in the pressure, can be reduced and high-accuracy analysis is made possible.

Since the valve 19 is also mounted on the movement mechanism, the channel from the valve 19 to the nozzle 2 can be short. While the cleaning liquid moving inside the channel can expand or contract depending on the temperature distribution, the expansion/contraction of the cleaning liquid occurring upstream of the valve 19 has no effect on the dispensing since the valve 19 is closed except when the cleaning is carried out. Since the capacity of the channel downstream of the valve 19 is small, the change in the amount of dispensing caused by the temperature distribution is small and high-accuracy analysis is possible.

Since the syringe 4 and the nozzle 2 are close to each other, the temperature difference can be kept small. Thus, dispensing hardly affected by temperature distribution is possible and high-accuracy analysis is made possible.

Since the valve 19 is mounted on the movement mechanism and the effect of the channel upstream of the valve 19 is weak, there are less restrictions on the arrangement of the cleaning liquid tube 61 and the ambient temperature distribution. Thus, the designing of the device is facilitated and a low-cost and small-sized device can be realized.

Incidentally, it is also possible to connect a replaceable and disposable dispensing tip to the end of the nozzle 2. By filling the channel with water, the dispensing can be conducted with high accuracy and contamination caused by the suction of liquid or soaking in liquid can be prevented.

As described above, according to this embodiment, the syringe 4 and the nozzle 2 are connected with each other by an elastic hollow-body member (connection tube 1). Thus, the pressure caused by the up-and-down movement of the plunger 13 of the syringe 4 can be transmitted to the end of the nozzle 2 and the dispensing function can be realized.

Further, since the driving source 6 is fixed on the syringe base 12' equipped with the syringe 4, the weight of the nozzle 2 as the movable part can be reduced and a greater upward displacement of the nozzle 2 with respect to a slighter load can be realized. Since even a slight load can be detected, high detection accuracy for the contact of the nozzle 2 can be achieved. Furthermore, since the clearance against the deforming load on the nozzle and the mechanism can also be set large, deterioration in the dispensing performance and malfunction of the mechanism caused by the deformation can be prevented.

Figure 20:
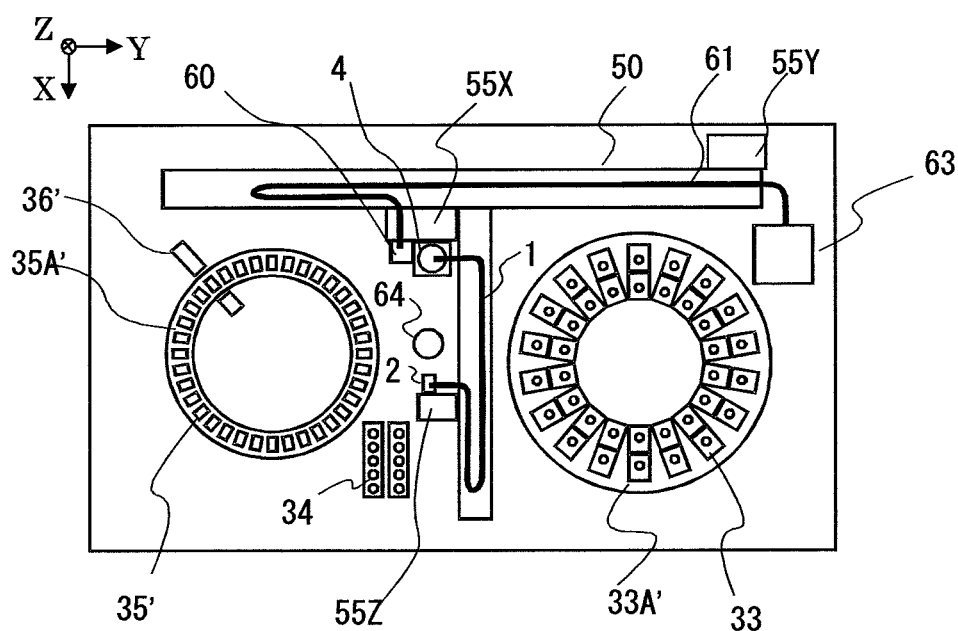
FIG. 20 is a plan view showing the configuration of an automatic analyzer equipped with a dispensing device in accordance with a sixth embodiment of the present invention.

Next, the configuration and operation of a dispensing device in accordance with a sixth embodiment of the present invention will be described with reference to FIG. 20. The following explanation will be given by taking an automatic analyzer for analyzing blood, etc. as an example of the automatic analyzer. FIG. 20 is a plan view showing the configuration of an automatic analyzer equipped with the dispensing device in accordance with the sixth embodiment of the present invention, wherein reference characters identical with those in FIG. 1 or 18 represent the same components as in FIG. 1 or 18.

The automatic analyzer shown in FIG. 20 uses liquid as the pressure-transmitting fluid.

The difference from the device shown in FIG. 18 is that the syringe 4 is attached to the X-axis movement mechanism 55X and the Z-axis movement mechanism 55Z held by the X arm 50X is moved in the X direction by the X-axis movement mechanism 55X. The syringe 4 and the nozzle 2 attached to the Z-axis movement mechanism 55Z are connected with each other by the connection tube 1. Also in this case, the nozzle 2 (corresponding to the movable unit) is connected to the X-axis movement mechanism 55X (corresponding to the fixed unit) via the X arm 50X and the Z-axis movement mechanism 55Z while also being relatively movable with respect to the fixed unit. The interior space of the syringe 4 attached to the fixed unit and the interior space of the nozzle 2 attached to the movable unit are connected with each other by the connection tube 1 having flexibility.

In this example, the Y-axis movement mechanism and the Z-axis movement mechanism 55Z are lightweight since no syringe is mounted thereon. Thus, the movement mechanisms can be implemented compact and at a low cost.

Since the connection tube 1 is filled with liquid, the amount of the discharge from the syringe 4 can be transmitted to the nozzle 2 correctly even if the connection tube 1 is long. Therefore, high-accuracy analysis is possible.

Since the syringe 4 is mounted on the movement mechanism 55X and the distance from the syringe 4 to the nozzle 2 is short, the connection tube 1 is allowed to be short and high-accuracy analysis can be conducted with high dispensing accuracy.

Since the syringe 4 and the valve 19 are mounted on the movement mechanism 55X, the effect of the expansion/contraction inside the cleaning liquid tube 61 extending to the movement mechanism 55X is weak. Thus, high-accuracy analysis with high dispensing accuracy is possible.

It is also possible to connect a replaceable and disposable dispensing tip to the end of the nozzle 2. By filling the channel with water, the dispensing can be conducted with high accuracy and contamination caused by the suction of liquid or soaking in liquid can be prevented.

Description of Reference Characters
1 connection tube
2 nozzle
3 connection rod
4 syringe
5 tip holding part
6 driving source
7 power converter
8 tip nozzle
9, 9U, 9L photo interrupter
11 detection plate
12 syringe base
13 plunger
14 syringe fixation member
15 spring
28, 29 elastic member
31 tip
33 reagent container
33A reagent container holding part
34 sample container
34A sample container holding part
35 reaction container
35A reaction container holding part

The invention claimed is:

1. A dispensing device, comprising:
   a syringe;
   a plunger inserted into the syringe;
   a tip nozzle configured to receive a tip replaceably attached to an end of a tip nozzle and configured to suck in liquid from a container and discharge the sucked liquid into another container by use of pressure generated by movement of plunger inserted into the syringe;
   a fixed unit;
   a movable unit which is connected to the fixed unit, the movable unit being relatively movable with respect to the fixed unit; and
   a movement mechanism which moves the fixed unit to and fro, wherein:
   the syringe and the plunger are held by the fixed unit, and the tip nozzle is attached to the movable unit, and
   the dispensing device comprises a connection tube having flexibility and connecting interior space of the syringe with interior space of the tip nozzle.

2. The dispensing device according to claim 1, further comprising detecting means which detects relative movement between the fixed unit and the movable unit.

3. The dispensing device according to claim 2, wherein the detecting means detects whether a tip attached to the tip nozzle has contacted another object based on the relative movement between the fixed unit and the movable unit.

4. The dispensing device according to claim 2, wherein the detecting means detects whether a tip has been attached to the tip nozzle based on the relative movement between the fixed unit and the movable unit.

5. The dispensing device according to claim 1, further comprising:
   a connection rod which slidably connects the movable unit to the fixed unit; and
   a spring, having an upper end and a lower end, arranged between the fixed unit and the movable unit,
   wherein the lower end of the spring contacts an upper end of the movable unit and the upper end of the spring has a noncontact spring length to a lower end of the fixed unit in a state in which the movable unit is suspended by the fixed unit.

6. The dispensing device according to claim 5, further comprising detecting means which detects relative movement between the fixed unit and the movable unit, wherein:
   the detecting means detects whether a tip attached to the tip nozzle has contacted another object by detecting the relative position between the upper end of the spring and the lower end of the fixed unit.

7. The dispensing device according to claim 1, further comprising an elastic member which connects the movable unit to the fixed unit,
   wherein the elastic member connects the movable unit to the fixed unit so that the movable unit is movable with respect to the fixed unit in at least two directions orthogonal to each other.

8. The dispensing device according to claim 1, further comprising:
   a connected space, from a hollow part within the syringe to an opening part at an end of a tip replaceably attached to the end of a tip nozzle, filled with air that is used as pressure-transmitting fluid for transmitting the pressure generated by the syringe.

9. The dispensing device according to claim 1, further comprising:
   a connected space, from a hollow part within the syringe to an opening part at an end of a tip replaceably attached to the end of a tip nozzle, filled with liquid that is used as pressure-transmitting fluid for transmitting the pressure generated by the syringe.

10. The dispensing device according to claim 1, wherein the movable unit is connected to the fixed unit so that the movable unit can rotate relative to the fixed unit to provide the tip nozzle at an angle with respect to vertical.

11. The dispensing device according to claim 5, further comprising detecting means which detects relative movement between the fixed unit and the movable unit, wherein:
   the detecting means detects that whether a tip has been attached to the tip nozzle in a state in which the spring has been compressed.

12. An analyzer comprising:
   a sample container holding part which holds a sample container storing a sample solution;
   a reagent container holding part which holds reagent containers storing reagents, respectively;
   a reaction container holding part which holds a reaction container;
   a dispensing device which sucks in the sample solution in the sample container and a prescribed reagent in the reagent container and dispenses the solutions to the reaction container; and
   a detector which detects the result of a reaction occurring in the reaction container,
   wherein the dispensing device includes:
   a fixed unit;
   a movable unit which is connected to the fixed unit, the movable unit being relatively movable with respect to the fixed unit; and
   a movement mechanism which moves the fixed unit to and fro,
   wherein:
   a syringe and a plunger are held by the fixed unit, and a tip nozzle or a nozzle is attached to the movable unit, and
   the dispensing device includes a connection tube having flexibility and connecting interior space of the syringe with interior space of the tip nozzle or the nozzle.

13. A dispensing device, comprising:
a syringe;
a plunger inserted into the syringe;
a nozzle configured to suck in liquid from a container and discharge the sucked liquid into another container by use of pressure generated by movement of plunger inserted into the syringe;
a fixed unit;
a movable unit which is connected to the fixed unit, the movable unit being relatively movable with respect to the fixed unit; and
a movement mechanism which moves the fixed unit to and fro, wherein:
the syringe and the plunger are held by the fixed unit, and the tip nozzle is attached to the movable unit, and
the dispensing device comprises a connection tube having flexibility and connecting interior space of the syringe with interior space of the tip nozzle.

14. The dispensing device according to claim 13, further comprising detecting means which detects relative movement between the fixed unit and the movable unit.

15. The dispensing device according to claim 14, wherein the detecting means detects whether the nozzle has contacted another object based on the relative movement between the fixed unit and the movable unit.

16. The dispensing device according to claim 13, further comprising an elastic member which connects the movable unit to the fixed unit,
wherein the elastic member connects the movable unit to the fixed unit so that the movable unit is movable in at least two directions orthogonal to each other.

17. The dispensing device according to claim 13, further comprising:
a connected space, from a hollow part within the syringe to an opening part at an end of the nozzle, filled with air that is used as pressure-transmitting fluid for transmitting the pressure generated by the syringe.

18. The dispensing device according to claim 13, further comprising:
a connected space, from a hollow part within the syringe to an opening part at an end of the nozzle, filled with liquid that is used as pressure-transmitting fluid for transmitting the pressure generated by the syringe.

19. The dispensing device according to claim 13, wherein the movable unit is connected to the fixed unit so that the movable unit can rotate relative to the fixed unit to provide the nozzle at an angle with respect to vertical.

* * * * *